United States Patent [19]
Lou et al.

[11] Patent Number: 5,965,350
[45] Date of Patent: Oct. 12, 1999

[54] CLONING AND EXPRESSION OF HUMAN GMP SYNTHETASE, ITS USE IN SCREENING FOR INHIBITORS OF HUMAN GMP SYNTHETASE AND INHIBITORS OF HUMAN GMP SYNTHETASE

[75] Inventors: Lillian Lien-Li Lou, Palo Alto; Jimmy Wayne Barnett, La Honda, both of Calif.

[73] Assignee: Syntex (U.S.A.) Inc., Palo Alto, Calif.

[21] Appl. No.: 08/224,917

[22] Filed: Apr. 8, 1994

[51] Int. Cl.[6] .............................. C12Q 1/25; C12N 9/00; C12N 15/52; C12N 15/70
[52] U.S. Cl. .......................... 435/4; 435/183; 435/69.1; 435/252.31; 435/320.1; 536/23.2; 935/14; 935/29; 935/73
[58] Field of Search .................................. 435/183, 69.1, 435/252.3, 320.1, 4; 536/23.2

[56] References Cited

U.S. PATENT DOCUMENTS 4,757,606  7/1988  Toole, Jr. et al. ...................... 435/69.1

FOREIGN PATENT DOCUMENTS 90-01545  2/1990  WIPO.

OTHER PUBLICATIONS

Page, T. et al., "Human GMP Synthetase", *Int. J. Biochem.*, (1984), 16, pp. 117–120.

Harai, K. et al., "Purification and Characterization of GMP Synthetase from Yoshida Sarcoma Ascites Cells", *J. Biochem.*, (1987), 102, pp. 893–902.

Spector, T. et al., "GMP Synthetase from Ehrlich Ascites Cells", *Methods Enzymology*, (1978), 51, pp. 219–224.

Tiedeman, A.A. et al., "Nucleotide Sequence of the guaA Gene Encoding GMP Synthetase of *Escherichia coli* K12", *J. Biol. Chem.*, (1985), 260, pp. 8676–8679.

Van Lookeren Campagne, M.M. et al., "Functional Cloning of a *Dictyostelium discoideum* cDNA Encoding GMP Synthetase", *J. Biol. Chem.*, (1991), 266, pp. 16448–16452.

Mantsala, P. et al., "Cloning and Sequence of *Bacillus subtilis purA* and *guaA*, Involved in the Conversion of IMP to AMP and GMP", *J. Bacteriology*, (1992), 174, pp. 1883–1890.

Spector, T. et al., "Guanosine Monophosphate Synthetase from Ehrlich Ascites Cells: Multiple Inhibition by Pyrophosphate and Nucleosides", *Biochimica et Biophysica Acta*, (1976), 452, pp. 597–607.

Saiki, R.K. et al., "Primer–Directed Enzymatic Amplification of DNA with a Thermostable DNA Polymerase", *Science*, (1989), 239, pp. 487–491.

(List continued on next page.)

Primary Examiner—Robert A. Wax
Assistant Examiner—William W. Moore
Attorney, Agent, or Firm—Heller Ehrman White & McAuliffe

[57] ABSTRACT

One aspect of the present invention is a purified human GMP synthetase and a method of purifying it from naturally occurring sources. Another aspect of the present invention is a recombinant human GMP synthetase as well as DNA sequences coding for human GMP synthetase, expression vectors comprising such a coding sequence, and host cells transformed with these expression vectors capable of producing human GMP synthetase. Also forming part of this invention is a recombinant process for the production of GMP synthetase. Further provided is a method of purifying GMP synthetase from natural or recombinant sources. Other aspects of the invention include antibodies to human GMP synthetase and the use of such antibodies to assay for human GMP synthetase. Another aspect of this invention is the use of purified naturally occurring human GMP synthetase or recombinant human GMP synthetase to identify inhibitors of GMP synthetase activity. Another aspect of the invention is inhibitors of human GMP synthetase activity obtained using purified human GMP synthetase. Such inhibitors preferably have an $IC_{50}$ of 5 $\mu$M or less, more preferably 1 $\mu$M or less.

6 Claims, 6 Drawing Sheets

OTHER PUBLICATIONS

Folks, T. et al., "Characterization of a continuous T–cell line susceptible to the cytopathic effects of the acquired immunodeficiency syndrome (AIDS)–associated retrovirus", *Proc. Natl. Acad. Sci. USA*, (1985), 82, pp. 4539–4543.

Eugui, E. M. et al., Antibodies against membrane interleukin 1α activate accessory cells to stimulate proliferation of T lymphocytes, *Proc. Natl. Acad. Sci. USA*, (1990), 87, pp. 1305–1309.

Taylor, A.L. et al., "Revised Linkage Map of *Escherichia coli*", *Bacteriol. Rev.*, (1967), 31, pp. 332–353.

Heller, R.A. et al., Complementary DNA cloning of a receptor for tumor necrosis factor and demonstration of a shed form of the receptor, *Proc. Natl. Acad. Sci. USA*, (1990), 87, pp. 6151–6155.

Chirgwin, J.M. et al., "Isolation of Biologically Active Ribonucleic Acid from Sources Enriched in Ribonuclease", *Biochemistry*, (1979), 18, pp. 5294–5299.

Aviv, H. et al., Purification of Biologically Active Globin Messenger RNA by Chromatography on Oligothymidylic acid–Cellulose, *Proc. Natl. Acad. Sci. USA*, (1972), 69, pp. 1408–1412.

Boritzki, T.J. et al., Guanosine–5'–Phosphate Synthetase and Guanosine–5'–Phosphate Kinase in Rat Hepatomas and Kidney Tumors, *Biochim. Biophys. Acta*, (1981), 658, pp. 102–110.

Wang, X. et al., "Baculovirus vectors for multiple gene expression and for occluded virus production", *Gene*, (1991), 100, pp. 131–137.

Mitchell, B.S. et al., IMP Dehydrogenase Inhibitors as Immunomodulators, *Ann. N.Y. Acad.Sci.*, (1993), 685, pp. 217–224.

Eugui, E.M. et al., Lymphocyte–Selective Cytostatic and Immunosuppressive Effects of Mycophenolic Acid in Vitro: Role of Deoxyguanosine Nucleotide Depletion, *Scand. J. Immunol.*, (1991), 33, pp. 161–173.

Eugui, E.M. et al., Immunosuppressive Activity of Mycophenolate Mofetil, *Ann. N.Y. Acad. Sci.*, (1993), 685, pp. 309–329.

Nakamura, J., et al., 1995, The Journal of Biological Chemistry, 270(13):7347–7353.

Weber, G., et al., 1983, Cancer Research, 43(3):1019–1023.

Bennett, L.L., et al., 1984, Biochemical Pharmacology, 33(2): 261–271.

Uchida, M., et al., 1985, Japan Journal of Cancer Research, 76(2):124–130.

Raju, N., et al., 1989, Journal of Medicinal Chemistry, 32(6):1307–1313.

Hirst, M., et al., 1994, The Journal of Biological Chemistry, 269(38):23830–23837.

Lathe, R., 1985, Journal of Molecular Biology 183(1):1–12.

Jaye, M., et al., 1983, Nucleic Acids Research, 11(8):2325–2335.

Ullrich, A., et al., 1984, The EMBO Journal, 3(2):361–364.

Dujardin, G., et al., 1994, Gene, 139(1):127–132.

Tabacchi, A., et al., 1990, Bolletino dela Societa–Italiana Biologio Sperimentale, 66(5): 449–455.

Kumar, Y., et al., 1993, Journal of Medicinal Chemistry, 36(24):3849–3852.

FIG. 1a

```
GAATTCGGCACGAGCTCCTCCTCCGCTGCCGCTGCTCCGACCAGGCCTCCTTCTCAACCTCAGCCC
GCGGGCCGACCCTTCCGGACACCCTCCCGCCCGTCGTCGCCGTCTGTCGCCGCACCGGCCCCTGGCCCCG
```

| ATG | GCT | CTG | TGC | AAC | GGA | GAC | TCC | AAG | CTG | GAG | AAT | GCT | GGA | GGA | GAC | CTT | AAG | GAT | GGC |
|-----|-----|-----|-----|-----|-----|-----|-----|-----|-----|-----|-----|-----|-----|-----|-----|-----|-----|-----|-----|
| M   | A   | L   | C   | N   | G   | D   | S   | K   | L   | E   | N   | A   | G   | G   | D   | L   | K   | D   | G   |

| CAC | CAC | TAT | GAA | GTG | AGG | GAA | CAA | TTC | GTC | ATT | CTG | GAT | GCT | GGT | GCT | CAG | TAC | GGG | AAA | GTC |
|-----|-----|-----|-----|-----|-----|-----|-----|-----|-----|-----|-----|-----|-----|-----|-----|-----|-----|-----|-----|-----|
| H   | H   | Y   | E   | V   | R   | E   | Q   | F   | V   | I   | L   | D   | A   | G   | A   | Q   | Y   | G   | K   | V   |

| ATA | GAC | CGA | AGA | GTG | AGG | GAA | CAA | TTC | CGT | GCT | GAT | CCA | AAT | ATT | TCT | GAA | ATT | TTC | CCC | TTG | GAA | ACA | CCA |
|-----|-----|-----|-----|-----|-----|-----|-----|-----|-----|-----|-----|-----|-----|-----|-----|-----|-----|-----|-----|-----|-----|-----|-----|
| I   | D   | R   | R   | V   | R   | E   | Q   | F   | R   | A   | D   | P   | N   | I   | S   | E   | I   | F   | P   | L   | E   | T   | P   |

| GCA | TTT | GCT | ATA | AAG | GAA | CAA | TTC | CGT | GCT | GAT | CCA | AAT | ATT | TCT | GGA | GGA | CCT | AAT | TCT |
|-----|-----|-----|-----|-----|-----|-----|-----|-----|-----|-----|-----|-----|-----|-----|-----|-----|-----|-----|-----|
| A   | F   | A   | I   | K   | E   | Q   | F   | R   | A   | D   | P   | N   | I   | S   | G   | G   | P   | N   | S   |

| GTG | TAT | GCT | GAA | GAT | GCT | CCC | TGG | TTT | ATG | CAG | GTT | TTC | AAC | ATT | ATC | ACT | ATT | GGC | AAG | CCT | GTT |
|-----|-----|-----|-----|-----|-----|-----|-----|-----|-----|-----|-----|-----|-----|-----|-----|-----|-----|-----|-----|-----|-----|
| V   | Y   | A   | E   | D   | A   | P   | W   | F   | M   | Q   | V   | F   | N   | I   | I   | T   | I   | G   | K   | P   | V   |

| CTT | GGA | ATT | TGC | TAT | GGT | ATG | CAG | GTT | GAT | GGA | GTG | AGT | ACA | CAT | GGA | GTA | GCA | ATA | GCA | ACT | GTG | CAC | AAA |
|-----|-----|-----|-----|-----|-----|-----|-----|-----|-----|-----|-----|-----|-----|-----|-----|-----|-----|-----|-----|-----|-----|-----|-----|
| L   | G   | I   | C   | Y   | G   | M   | Q   | V   | D   | G   | V   | S   | T   | H   | G   | V   | A   | I   | A   | T   | V   | H   | K   |

| AAA | AGT | GTC | AGA | GAA | GAT | GGA | GAT | GGA | GAA | GAA | GTT | GTG | GCA | CAG | TTC | TAT | GAT | ATA | CGA | ATC | GAG | AAA | ATC | AAA | GAA | AAT | GGA | AAA |
|-----|-----|-----|-----|-----|-----|-----|-----|-----|-----|-----|-----|-----|-----|-----|-----|-----|-----|-----|-----|-----|-----|-----|-----|-----|-----|-----|-----|-----|
| K   | S   | V   | R   | E   | D   | G   | N   | D   | E   | V   | V   | A   | Q   | F   | Y   | D   | I   | R   | I   | E   | K   | I   | K   | E   | N   | G   | K   |

| AGG | GGC | CTT | CAG | AAG | GAA | GAA | GTT | GTG | GCA | CAG | TTC | TAT | GAT | ATA | CGA | ATC | CGA | AAA | ATC | AAA | GAA | AAT | GGA | AAA |
|-----|-----|-----|-----|-----|-----|-----|-----|-----|-----|-----|-----|-----|-----|-----|-----|-----|-----|-----|-----|-----|-----|-----|-----|-----|
| R   | G   | L   | Q   | K   | E   | E   | V   | V   | A   | Q   | F   | Y   | D   | I   | R   | I   |     |     |     |     |     |     |     |     |

| GCT | GAT | GGA | TTC | AAG | GTT | GTG | GCA | CGT | TCT | GGA | TCT | CAC | CCT | GAA | GCT | ATA | AAA | ATC | CGA | GAG | ATC | AAA | AAA | GCA | ATA | GCA | AAT | GAA |
|-----|-----|-----|-----|-----|-----|-----|-----|-----|-----|-----|-----|-----|-----|-----|-----|-----|-----|-----|-----|-----|-----|-----|-----|-----|-----|-----|-----|-----|
| A   | D   | G   | F   | K   | V   | V   | A   | R   | S   | G   | S   | H   | P   | E   | A   | I   | K   |     |     |     |     | A   | I   | A   | N   | E   |

(1)

| TCT | AAA | AAG | TTA | TAT | GGA | GCA | CAG | TTC | CAC | CCT | GAA | GTT | GGC | CTT | ACA | GAA | AAT | GGA | AAA |
|-----|-----|-----|-----|-----|-----|-----|-----|-----|-----|-----|-----|-----|-----|-----|-----|-----|-----|-----|-----|
| S   | K   | K   | L   | Y   | G   | A   | Q   | F   | H   | P   | E   | V   | G   | L   | T   | E   | N   | G   | K   |

| GTA | ATA | TTC | AAG | AAT | TTC | CTT | TAT | GAT | ATA | TTC | CGA | ATC | GCT | AAA | GCT | GGA | ACC | TTC | ACC | GTG | CAG |
|-----|-----|-----|-----|-----|-----|-----|-----|-----|-----|-----|-----|-----|-----|-----|-----|-----|-----|-----|-----|-----|-----|
| V   | I   | F   | K   | N   | F   | L   | Y   | D   | I   | F   | R   | I   | A   | K   | G   | T   | F   | T   | V   | Q   |

| AAC | AGA | GAA | CTT | GAG | TGT | ATT | CGA | GAG | ATC | AAA | AAA | GAG | TCA | GAC | ACG | ACA | AAA | GTT | TTG |
|-----|-----|-----|-----|-----|-----|-----|-----|-----|-----|-----|-----|-----|-----|-----|-----|-----|-----|-----|-----|
| N   | R   | E   | L   | E   | C   | I   | R   | E   | I   | K   | K   | E   | S   | D   | T   | T   | K   | V   | L   |

| GTT | TTA | CTC | AGT | GGT | GGA | GTA | GAC | TCA | ACA | GTT | TGT | ACA | GCT | TTG | CTA | AAT | CGT | GCT | TTG |
|-----|-----|-----|-----|-----|-----|-----|-----|-----|-----|-----|-----|-----|-----|-----|-----|-----|-----|-----|-----|
| V   | L   | L   | S   | G   | G   | V   | D   | S   | T   | V   | C   | T   | A   | L   | L   | N   | R   | A   | L   |

```
 25
AAC CAA GAA CAA GTC ATT GCT GTG CAC ATT GAT AAT GGC TTT ATG AGA AAA CGA GAA AGC
 N   Q   E   Q   V   I   A   V   H   I   D   N   G   F   M   R   K   R   E   S

CAG TCT GTT GAA GAG GCC CTC AAA AAG CTT GGA ATT CAG TTT ATG AAA GTG ATA AAT GCT GCT
 Q   S   V   E   E   A   L   K   K   L   G   I   Q   F   M   K   V   I   N   A   A
                                                                      (3)

CAT TCT TTC TAC AAT GGA ACA ACC ATG AAT ATG ACC CTA CCA ATA TCA GAT GAA ACC CCA CGG
 H   S   F   Y   N   G   T   T   M   N   M   T   L   P   I   S   D   E   T   P   R

AAA AGA ATT AGC AAA ACG TTA AAT GCC ACA GTA ATT GGA GAA ATG AAC TTG AAA AGA ATC ATT
 K   R   I   S   K   T   L   N   A   T   V   I   G   E   M   N   L   K   R   I   I
                                        (5)                                  (4)

GGG GAT ACT TTT GTT AAG ATT CGG CCT GAT CTA ATT GAA AGT GCA TCC CTT GAG CCA GAG
 G   D   T   F   V   K   I   R   P   D   L   I   E   S   A   S   L   V   P   E

GAG GTT CTT GCC CAA GGT ACT AAA ACC CAT CAC AAT GAC ACA GAG CTC AGA AAG GTT
 E   V   L   A   Q   G   T   K   T   H   H   N   D   T   E   L   R   K   V

GCA AGT GCT GAA CTC ATC ATA AAA CCT CTG AAA GAT TTT CAT CCA TTT CCA ATC GAT GAA GTG AGA
 A   S   A   E   L   I   I   K   P   L   K   D   F   H   P   Y   I   C   D   E   V   R

TTG AGA GAG GGA AAA GTA ATA GAG GAG TTA GTT TCC AGG CAT CCA TTT AAG GAC TTT CCT
 L   R   E   G   K   V   I   E   E   L   V   S   R   H   P   F   K   D   F   P
              (6)                                         (7)

ATT TTG GGC AGA GAA CTT GGA GTA ATA CCT GAA GAA TTT TCT TAT ATT TGT GCA AGT CAG CAG ATG CAA
 I   L   G   R   E   L   G   V   I   P   E   E   F   S   Y   I   C   A   S   Q   Q   M   Q

CCT GGC CTG GCA ATC AGA TTG AAA GCC GAT GCT ACA GAA GAG TTT TCT GCA GAT GAG AAG CTG GGT GTG CAG
 P   G   L   A   I   R   L   K   A   D   A   T   E   E   F   S   A   D   E   K   L   G   V   Q

GAA ACC AAC AAT ATT TTA CAG AGA GTC AAA GCC TGC TCA ACA ACC TTC CTG CCA ATT AAG CCA CAT
 E   T   N   N   I   L   Q   R   V   K   A   C   S   T   T   F   L   P   I   K   P   H

ACC CTA TTA AGT CTG CAT TCA CTG AAT GCC TTC TTG CTG CCA ATT AAG AGT AAA ACT GTA GGT GTG CAG
 T   L   L   S   L   H   S   L   N   A   F   L   L   P   I   K   S   K   T   V   G   V   Q

ATT ACC AGT CTG CAT TCA CTG AAT GCC TTC TTG CTG CCA ATT AAG AGT AAA ACT GTA GAT GAA CCT GAC TGG
 I   T   S   L   H   S   L   N   A   F   L   L   P   I   K   S   K   T   V   D   E   P   D   W

GGT GAC TGT CGT TAC TCC AGT TAC GTG TGT GGA ATC TCC AGT AAA GAT GAA CCT GAC TGG
 G   D   C   R   Y   S   S   Y   V   C   G   I   S   S   K   D   E   P   D   W
```

FIG. 1c

```
GAA TCA CTT ATT TTT CTG GCT AGG CTT ATA CCT CGC ATG TGT CAC AAC GTT AAC AGA GTT
 E   S   L   I   F   L   A   R   L   I   P   R   M   C   H   N   V   N   R   V

GTT TAT ATA TTT GGC CCA CCA GTT AAA GAA CCT ACA GAT GTT ACT CCC ACT TTC TTG
 V   Y   I   F   G   P   P   V   K   E   P   T   D   V   T   P   T   F   L

ACA ACA GGG GTG CTC AGT ACT CGC CAA GCT GAT TTT GAG GCC CAT AAC ATT CTC AGG
 T   T   G   V   L   S   T   L   R   Q   A   D   F   E   A   H   N   I   L   R

GAG TCT GGG TAT GCT GGG AAA CAG ATC AGC CAG ATG CCG GTG ATT TTG ACA CCA TTA CAT TTT
 E   S   G   Y   A   G   K   Q   I   S   Q   M   P   V   I   L   T   P   L   H   F

GAT CGG GAC CCA CTT CAA AAG CAG CCT TCA TGC CAG AGA TCT GTG GTT ATT CGA ACC T
 D   R   D   P   L   Q   K   Q   P   S   C   Q   R   S   V   V   I   R   T   F (8)
                                                                              ___

ATT ACT AGT GAC TTC ATG ACT GGT ATA CCT GCA ACA CCT GGC AAT GAG ATC CCT GTA GAG
 I   T   S   D   F   M   T   G   I   P   A   T   P   G   N   E   I   P   V   E
         8s                                                 (9)
                                                            ___

GTG GTA TTA AAG ATG GTC ACT GAG ATT AAG AAG ATT CCT GGT ATT TCT CGA ATT ATG TAT
 V   V   L   K   M   V   T   E   I   K   K   I   P   G   I   S   R   I   M   Y

GAC TTA ACA TCA AAG CCC CCA GGA ACT ACT GAG TGG GAG TAATAAACTTC
 D   L   T   S   K   P   P   G   T   T   E   W   E
```

CLONING AND EXPRESSION OF HUMAN GMP SYNTHETASE, ITS USE IN SCREENING FOR INHIBITORS OF HUMAN GMP SYNTHETASE AND INHIBITORS OF HUMAN GMP SYNTHETASE

BACKGROUND OF THE INVENTION

1. Field of the Invention

This invention relates to purified human GMP synthetase, its production by recombinant technology and nucleic acid sequences encoding for human GMP synthetase and its use in assaying for inhibitors of human GMP synthetase activity and the inhibitors identifiable by such assays.

Human guanosine 5'-monophosphate (GMP) synthetase is a key enzyme in the de novo synthesis of guanine nucleotides. Biosynthesis of guanine nucleotides is not only essential for deoxyribonucleic acid (DNA) and ribonucleic acid (RNA) synthesis, but also for providing guanosine 5'-triphosphate (GTP) which is involved in a number of cellular processes important for cell division. GTP hydrolysis is required for microtubule assembly, protein glycosylation, synthesis of adenine nucleotides, protein translation and activation of G proteins. A key step in the de novo synthesis of guanine nucleotides is the conversion of inosine 5'-monophosphate (IMP) to guanosine 5'-monophosphate (GMP). Two enzymes are involved in converting IMP to GMP: IMP dehydrogenase (EC 1.1.1.205) which catalyzes the oxidation of IMP to XMP (xanthine 5'-monophosphate) and GMP synthetase (EC 6.3.5.2.) which catalyzes the amination of XMP to GTP. The reaction catalyzed by GMP synthetase is:

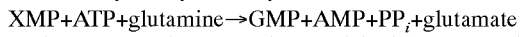

Both GMP synthetase and IMP dehydrogenase exhibit elevated levels of activity in rapidly proliferating cells, such as neoplastic and regenerating tissues. Inhibition of GMP synthetase or IMP dehydrogenase has been shown to result in the inhibition of cell growth. Because of this antiproliferative effect of GMP synthetase and IMP dehydrogenase inhibitors, both enzymes are potential targets for anticancer and immunosuppressive therapies. In fact, in recent clinical trials, a potent inhibitor of IMP dehydrogenase, mycophenolic acid, was shown to be effective in treatment of transplant rejection and rheumatoid arthritis.

The inhibition of lymphocyte proliferation by mycophenolic acid is closely correlated with the lowering of the intracellular pool of guanine nucleotides. Furthermore, this inhibition of proliferation can be blocked by the addition of exogenous guanosine. These data suggest that the immunosuppressive activity of mycophenolic acid is a result of the depletion of the guanine nucleotide pool. Since GMP synthetase is crucial for the de novo synthesis of guanine nucleotides, the inhibition of GMP synthetase should also result in the depletion of guanine nucleotides and therefore could be a target for immunosuppressive and cancer therapies.

Despite its significance, the information available for human GMP synthetase is limited. Heretofore, the human enzyme has not been obtained in a purified state. Even though a partially purified preparation from human fibroblast cells (T. Page, B, Bakay and W. L. Nyhan; *Int. J. Biochem.*, 16, 117–120, (1984)) has been reported, it contained varying amounts 5'-nucleotidase, purine nucleoside phosphorylase, and GMP kinase. The degree of purification of the enzyme was approximately 50-fold over the naturally occurring material and its specific activity was reported to be 5990 pmoles guanine compound produced/min/mg. By contrast, the present invention discloses a purified human GMP synthetase purified 936-fold over the naturally occurring material with a specific activity of at least 2,500,000 pmoles adenosine 5'-monophosphate (AMP) produced/min/mg. GMP synthetases of mammalian origin have been isolated in varying degrees of purity from a variety of sources. However, mammalian GMP synthetases, even if available in a high degree of purity, are of limited utility in screening for inhibitors for the purposes of human therapy.

Genetic information for human GMP synthetase is not available. Although the cDNA for GMP synthetase has been isolated from *E. coli*, *B. subtilis* and *D. discoideum*, no human or mammalian cDNAs or genes for GMP synthetase are available. Therefore it has not been possible to produce human GMP synthetase by recombinant DNA technology.

Accordingly, human GMP synthetase has not been available in a form suitable either for elucidation of its mechanism or for its use in screening for potential inhibitors. Neither has there been sequence information such as, for example, cDNA sequences coding for human GMP synthetase which would enable the production of human GMP synthetase by recombinant DNA technology. For these reasons, it is desirable to produce pure, well characterized human GMP synthetase in large quantities for the purposes, for example, of elucidating the mechanisms of its activity, identifying its role in various disease states and screening for therapeutically significant inhibitors of guanine nucleotide biosynthesis. Furthermore, it would be desirable to produce human GMP synthetase by means of recombinant DNA technology because it would make the enzyme available in much larger amounts than is practical in purification from natural sources.

2. Summary of Related Art

Human GMP Synthetase; T. Page, B, Bakay and W. L. Nyhan; *Int. J. Biochem.*, 16, 117–120, (1984); disclosed GMP synthetase from human fibroblasts, purified approximately 50-fold by ammonium sulfate fractionation and gel filtration.

Purification and Characterization of GMP Synthetase from Yoshida Sarcoma Ascites Cells; K. Harai, Y. Matsuda and H. Nakagawa; *J. Biochem.*, 102, 893–902, (1987); disclosed GMP synthetase purified from Yoshida Sarcoma mouse ascites cells by means of procedures including centrifugal fractionation. The purified enzyme was shown to be homogeneous on SDS-polyacrylamide gel electrophoresis and isoelectric focusing in polyacrylamide gel.

GMP Synthetase from Ehrlich Ascites Cells; T. Spector; *Methods Enzymology*, 51, 219–224, (1978); described coupled spectrophotometric and radiochemical assays for measuring GMP synthetase. The formation of AMP and/or GMP is coupled to the oxidation of NADH as mediated via AMP kinase and/or GMP kinase, pyruvate kinase, and lactate dehydrogenase.

Nucleotide Sequence of the guaA Gene Encoding GMP Synthetase of *Escherichia coli* K12; A. A. Tiedeman, J. M. Smith and H. Zalkin; *J. Biol. Chem.* 260, 8676–8679, (1985); reported the cloning and DNA sequence of a 1.7-kilobase pair BanII-PvuII fragment containing the *E. coli* guaA structural gene. A single open reading frame of 1575 nucleotides was found and sequenced. The deduced amino acid sequence contained 525 residues having a calculated subunit $M_T$ of 58,604.

Functional Cloning of a *Dictyostelium discoideum* cDNA Encoding GMP Synthetase; M. M. Van Lookeren Campagne, J. Franke and R. H. Kessin; *J. Biol. Chem.* 266, 16448–16452 (1991); disclosed a functional cloning procedure to recover a cDNA coding for the GMP synthetase of

*Dictyostelium discoideum*. The enzyme is encoded by a single gene. The open reading frame encodes a protein of 718 amino acids with a predicted molecular mass of 79.6 kDa.

Cloning and Sequence of *Bacillus subtilis* purA and guaA, Involved in the Conversion of IMP to AMP and GMP; P. Mantsala and H. Zalkin; *J. Bacteriology* 174, 1883–1890 (1992); disclosed the nucleotide sequences of the *Bacillus subtilis* genes purA, encoding adenylosuccinate synthetase, and guaA, coding for GMP synthetase. The sequences were determined from a series of gene fragments isolated by polymerase chain reaction amplification, library screening and plasmid rescue techniques.

Guanosine Monophosphate Synthetase from Ehrlich ascites cells: Multiple inhibition by pyrophosphate and nucleosides; T. Spector, T. E. Jones, T. A. Krenitsky and R. J. Harvey; *Biochimica et Biophysica Acta* 452, 597–607 (1976); disclosed nucleoside inhibitors of GMP synthetase from Ehrlich ascites cells as well as the inhibition of the enzyme by its reaction product, pyrophosphate.

SUMMARY OF THE INVENTION

One aspect of the present invention is a purified human GMP synthetase and a method of purifying it from naturally occurring sources. The method comprises homogenizing host cells producing human GMP synthetase, isolating the cytosolic component, fractionating the cytosolic component to its protein fraction and subjecting the protein component to chromatographic purification.

Another aspect of the present invention is a recombinant human GMP synthetase as well as DNA sequences coding for human GMP synthetase, expression vectors comprising such a coding sequence, and host cells transformed with these expression vectors capable of producing human GMP synthetase. In one aspect, the invention includes a nucleic acid molecule included in, or derived from, the sequence: (GMPS.6 (SEQ ID NO: 1)), which is capable of encoding for human GMP synthetase.

Another aspect of the invention is sets of degenerate polynucleotide primers corresponding to spaced amino acid sequences of human GMP synthetase for use in selectively amplifying human derived nucleic acid sequences which code for GMP synthetase. Each set of primers contains substantially all of the possible coding sequences corresponding to the spaced amino acid sequences of human GMP synthetase. That is, each set includes at least one primer species that can effectively hybridize with the coding sequence of the corresponding amino acid region.

Further aspects of this invention include polynucleotide probes capable of hybridizing to nucleic acid sequences contained within the nucleic acid sequence of human GMP synthetase as well as such polynucleotide probes labeled with at least one reporter molecule. Also included within this invention are assays for DNA sequences encoding for human GMP synthetase using such labeled or unlabeled polynucleotide probes.

Also forming part of this invention is a recombinant process for the production of GMP synthetase. This recombinant process involves inserting a DNA sequence encoding for GMP synthetase into an expression vector, transforming a suitable host with the vector and isolating the recombinant protein expressed by the vector.

Further provided is a method of purifying GMP synthetase from natural or recombinant sources. This method comprises the steps of homogenizing cells expressing human GMP synthetase and isolating the cytosolic component, fractionating the cytosolic component to its protein fraction and subjecting the protein fraction to chromatographic purification.

Other aspects of the invention include antibodies to human GMP synthetase and the use of such antibodies to assay for human GMP synthetase.

Another aspect of this invention is the use of purified naturally occurring human GMP synthetase or recombinant human GMP synthetase to identify inhibitors of GMP synthetase activity. In this aspect an assay is carried out by a method comprising contacting a medium suspected of containing one or more of such inhibitors with purified human GMP synthetase and measuring the activity of the human GMP synthetase.

Another aspect of the invention is inhibitors of human GMP synthetase activity obtained using purified human GMP synthetase. Such inhibitors preferably have an $IC_{50}$ of 5 $\mu$M or less, more preferably 1 $\mu$M or less, and find use in inhibiting human GMP synthetase activity.

BRIEF DESCRIPTION OF THE DRAWINGS

FIG. 1. Nucleotide and predicted amino acid sequences of human GMP synthetase.
Amino acid residues are represented in single-letter code. Lines and numbers in parentheses mark the position of sequences corresponding to the tryptic peptides determined from the purified native enzyme. Boxes mark the position of sequences corresponding to the oligonucleotide primers. Nucleotide residue 1 represents the start site of translation.

DETAILED DESCRIPTION OF THE INVENTION

Figure 2:
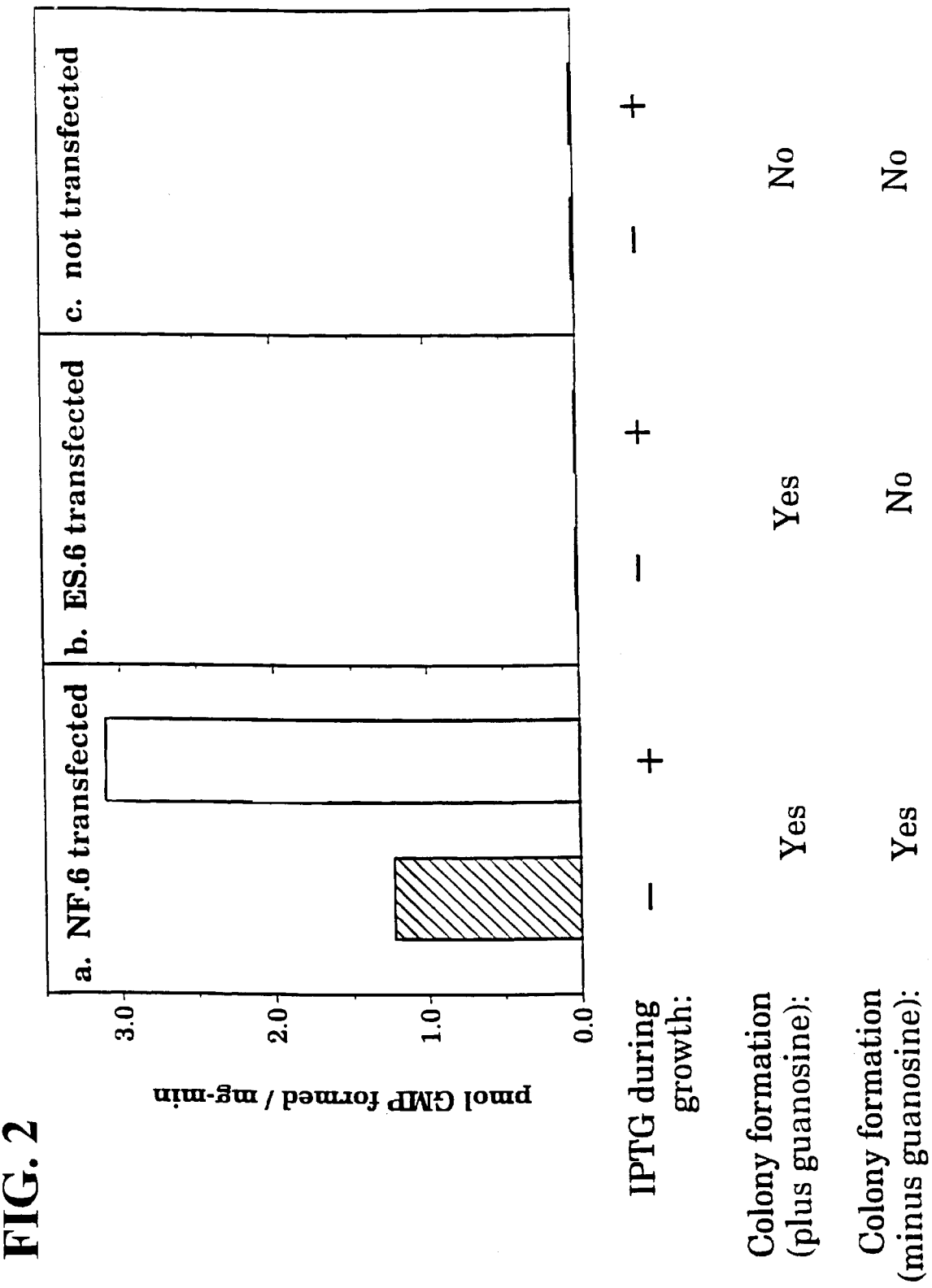
FIG. 2. Functional expression of GMPS.6 (SEQ ID NO: 1) in a GMP synthetase deficient strain of *E. coli*.
The expression vectors NF.6 and ES.6 were transfected into AT2465 *E.coli*, and the cultures were spread on minimal media plates with or without guanosine as described in Example 2. Colony formation was monitored after 24 hours. To determine GMP synthetase activity, single colonies were selected, propagated and induced with IPTG, as described in Example 2. Single colonies were selected from "minus guanosine" plates with NF.6 transfected cells and from "plus guanosine" plates with ES.6 transfected cells. Single colonies of cells that were not transfected were selected from LB plates. Cultures were harvested and the cytosolic fractions were assayed for GMP synthetase activity as described in Example 2.

The present invention includes purified naturally occurring and recombinant human GMP synthetase as well as methods of purifying human GMP synthetase from cells expressing human GMP synthetase. Further included are recombinant processes for the production of human GMP synthetase. The invention also includes nucleic acid sequences coding for human GMP synthetase, expression vectors comprising this coding sequence and host cells transformed with these expression vectors capable of expressing human GMP synthetase. Also included are polynucleotide probes capable of hybridizing to nucleic acid sequences of human GMP synthetase and assays for human GMP synthetase using such probes. Also included are antibodies to human GMP synthetase, assays for GMP synthetase using such antibodies and assays for inhibitors of human GMP synthetase activity using the recombinant or purified natural enzyme disclosed by this invention. The invention also includes inhibitors of human GMP synthetase preferably having an $IC_{50}$ of 5 $\mu$M or less.

Before proceeding further with the description of the specific embodiments of the invention a number of terms will be defined.

The term "purified human GMP synthetase" refers to a human GMP synthetase which is essentially free, i.e. contains less than about 30%, preferably less than about 10%, and even more preferably less than about 95% of the proteins with which the human GMP synthetase is naturally associated. Techniques for assessing purity are well known to the art and include, for example, sodium dodecyl sulfate (SDS) gel electrophoresis, high pressure liquid chromatography (HPLC), isoelectric focusing and capillary gel electrophoresis. Thus, the term purified also refers to a human GMP synthetase which appears as essentially one band on SDS gel electrophoresis when visualized by Coomassie blue staining. Purity can alternatively be assessed by measurement of the activity of the human GMP synthetase, for example, by the rate at which the purified human GMP synthetase produces adenosine 5'-monophosphate (AMP). Thus, the term purified may also refer to a human GMP synthetase that produces AMP at a rate at least 100 fold faster than, preferably 500 fold faster than, and more preferably 900 fold faster than, the human GMP synthetase in its naturally occurring state when measured under the conditions disclosed herein. The term purified can also refer to a human GMP synthetase that has a specific activity of at least 2.5 $\mu$moles (2,500,000 pmoles) of AMP produced/min/mg when enzyme activity is measured using the conditions described in Example 1. The activity of the human GMP synthetase is measured by determining the rate at which it catalyzes the conversion of XMP to GMP or ATP to AMP under the conditions described in the Examples 1 and 3.

The term "$IC_{50}$" refers to the concentration of a compound that is required to inhibit by 50% the activity of purified human GMP synthetase when enzyme activity is measured under the conditions of the procedure # 2, the radioactive assay, described in Example 5. Briefly, the assay measures the conversion of XMP to GMP or ATP to AMP in the presence or absence of a suspected inhibitory compound. Therefore, the concentration of the inhibitory compound in the assay that reduces the amount of GMP or AMP produced by 50% compared to the amount of GMP or AMP produced in the absence of the compound is the $IC_{50}$ of that compound.

The term "polynucleotidel " as used herein refers to a polymeric form of nucleotides of any length, either ribonucleotides or deoxyribonucleotides. This term refers only to the primary structure of the molecule. Thus, this term includes double and single stranded DNA, as well as double and single stranded RNA. It also includes modified, for example, by methylation and/or by capping, and unmodified forms of the polynucleotide.

The term "recombinant polynucleotide" as used herein refers to a polynucleotide of genomic, cDNA, semisynthetic or synthetic origin which, by virtue of its origin or manipulation: (1) is not associated with all or a portion of the polynucleotide with which it is associated in nature and/or (2) is linked to a polynucleotide other than that to which it is linked in nature.

The term "cDNA" or complementary DNA refers to single stranded or double stranded DNA sequences obtained by reverse transcription of messenger RNA isolated from a donor cell. For example, treatment of messenger RNA with a reverse transcriptase such as AMV reverse transcriptase or M-MuLV reverse transcriptase in the presence of an oligonucleotide primer will furnish an RNA-DNA duplex which can be treated with RNase H, DNA polymerase and DNA ligase to generate double stranded cDNA. If desired, the double stranded cDNA can be denatured by conventional techniques such as shearing to generate single stranded cDNA.

An "expression vector" is any genetic element, e.g., a plasmid, a chromosome, a virus, behaving either as an autonomous unit of polynucleotide replication within a cell (i.e. capable of replication under its own control) or being rendered capable of replication by insertion into a host cell chromosome, having attached to it another polynucleotide segment, so as to bring about the replication and/or expression of the attached segment. Suitable vectors include, but are not limited to, plasmids, bacteriophages and cosmids. Vectors will contain polynucleotide sequences which are necessary to effect ligation or insertion of the vector into a desired host cell and to effect the expression of the attached segment. Such sequences differ depending on the host organism; they include promoter sequences to effect transcription, enhancer sequences to increase transcription, ribosomal binding site sequences and transcription and translation termination sequences.

The term "transfer vector" refers to a plasmid that enables the integration of a recombinant gene into virus DNA by homologous recombination.

The term "host cell" generally refers to prokaryotic or eukaryotic organisms and includes any transformable organism which is capable of expressing a protein and can be, or has been, used as a recipient for expression vectors or other transfer DNA.

The term "transformed" refers to any known method for the insertion of foreign DNA sequences into a host cell whereby the inserted DNA is rendered capable of replication in the host cell. The transformation procedure depends on the host cell being transformed. It can include packaging the polynucleotide in a virus as well as direct uptake of the polynucleotide. Transformation can result in incorporation of the inserted DNA into the genome of the host cell or the maintenance of the inserted DNA within the host cell in plasmid form. Methods of transformation are well known in the art and include, but are not limited to, viral infection, electroporation, lipofection and calcium phosphate mediated direct uptake.

It is to be understood that this invention is intended to include other forms of expression vectors, host cells and transformation techniques which serve equivalent functions and which become known to the art hereto.

The term "cDNA library" refers to a collection of host cells transformed with cDNA sequences derived from a donor cell.

The term "reporter molecule" refers to a chemical entity capable of being detected by a suitable detection means, including, but not limited to, spectrophotometric, immunochemical, or radiochemical means.

The term a polynucleotide "derived from" a designated sequence, for example, the GMPS.6 sequence depicted in FIG. 1, which includes the cDNA of human GMP synthetase, refers to a polynucleotide sequence which is comprised of a sequence of approximately at least 6 nucleotides, preferably at least 8 nucleotides, more preferably at least 10–12 nucleotides, and, even more preferably, at least 15–20 nucleotides corresponding to, i.e., homologous or complementary to, a region of the designated sequence. The derived polynucleotide sequence is not necessarily physically derived from the nucleotide sequence shown, but may be derived in any manner, including for example, chemical synthesis or DNA replication or reverse transcription, which are based on the information provided by the sequences of bases in the region(s) from which the polynucleotide is derived.

The term "inhibitor" refers to a compound or extract which decreases the enzyme activity of human GMP synthetase when enzyme activity is measured in the presence of the inhibitor relative to the enzyme activity measured in the absence of the inhibitor. Specific methods of measuring enzyme activity in the presence of suspected inhibitors are described more fully in Example 5.

Purification of human GMP synthetase

The general method of purifying human GMP synthetase by the method of this invention comprises the steps of cell lysis, homogenization, centrifugation, anion exchange chromatography, hydrophobic interaction chromatography, and high resolution anion exchange chromatography.

Typically, a human cell line such as, for example, a T-lymphoblastoma cell line, a Jurkat cell line, or a B cell line expressing GMP synthetase is cultured under conditions appropriate to the particular cell line being used in an appropriate aqueous medium. The invention is not restricted to any particular types of human cell lines although transformed cell lines may provide better results than tissue. The medium will usually be a salt medium such as normal saline, phosphate buffer, or phosphate buffered saline containing additives well known to those skilled in the art and commercially available from a number of suppliers such as GIBCO and Hyclone. The cultured cells are then homogenized under conventional conditions such as, for example, sonication, freeze-thawing, and hypotonic lysis, and the cytosolic fraction is obtained by centrifugation and recovery of the supernatant. Differential salt fractionation, using, for example, ammonium sulfate, is employed to separate the GMP synthetase-rich protein fraction. Salt is then removed by one of a variety of known methods such as gel filtration, dialysis and the like. The desalted protein fraction is then subjected to anion exchange chromatography. This is preferably done using DEAE-cellulose or Q-Sepharose as examples of anion exchange material. Fractions showing GMP-synthetase activity are further subjected to hydrophobic interaction chromatography and a second purification via anion exchange chromatography. GMP synthetase activity is measured by the spectrophotometric-coupled assay described by Spector (T. Spector; *Methods Enzymology*, 51, 219–224, (1978)). The assay measures the rate of production of AMP by GMP synthetase by coupling it to the oxidation of NADH via the auxiliary enzymes AMP kinase, pyruvate kinase and lactate dehydrogenase. In this fashion a purified human GMP synthetase is obtained. It has a molecular weight of approximately 75 kDa and is a single band on SDS gel electrophoresis when visualized by Coomassie blue staining. Furthermore, it has a specific activity of 2.5 $\mu$moles AMP produced/min/mg or greater, often in the range 2.5 to 4.0 $\mu$moles AMP produced/min/mg, in the spectrophotometric-coupled Spector assay referenced above.

Recombinant human GMP synthetase

As described above, the present invention provides purified human GMP synthetase. Purified human GMP synthetase may be used to design DNA probes for obtaining genomic or cDNA clones for use in the recombinant production of human GMP synthetase. For example, the amino acid sequence of purified protein can be determined by chemical techniques and oligonucleotide sequences coding for specific amino acid segments can be derived. Alternatively, the purified protein can first be subjected to enzymatic digestion using proteases such as trypsin, pepsin and the like to obtain peptide fragments whose amino acid sequences can be determined by techniques such as Edman degradation.

These amino acid sequences are used to construct oligonucleotide primers of complementary sequences which may be used in a polynucleotide amplification technique such as the polymerase chain reaction (PCR) (R. K. Saiki, D. H. Gelfand, S. Stoffel, S. J. Scharf, R. Higuchi, G. T. Horn, K. B. Mullis, and H. A. Ehrlich, *Science*, 239, 487–491 (1989) to amplify cDNA from a human cell line to obtain a DNA sequence included within the gene coding for human GMP synthetase. Due to the degeneracy of the genetic code, oligonucleotide primers of complementary sequences are customarily prepared in all possible variations. On occasion, variation of the primer sequences may be limited based on homology with related enzymes and/or species specific codon usage. The identity of the DNA sequence obtained via amplification can be verified by subcloning into a second vector and sequencing positive clones to establish the presence of sequences corresponding to the originally used oligonucleotide primers. This DNA sequence obtained as above can then be used to screen a cDNA library obtained from a human cell line expressing GMP synthetase to identify the complete nucleic acid sequence coding for the enzyme.

The basic molecular biology techniques employed in accomplishing features of this invention, such as RNA and DNA and plasmid isolation, restriction enzyme digestion, preparation and probing of a cDNA library, sequencing clones, constructing expression vectors, transforming cells, maintaining and growing cell cultures and other general techniques are well known in the art, and descriptions of such techniques can be found in general laboratory manuals such as *Molecular Cloning: A Laboratory Manual* by J. Sambrook, E. F. Fritsch and T. Maniatis, published by the Cold Spring Harbor Laboratory Press, 2nd edition, 1989.

The DNA sequences contemplated by this invention comprise oligodeoxynucleotides coding for human GMP synthetase as well as fragments thereof, as well as all equivalent nucleotide sequences coding for molecules with substantially the same human biological activity as human GMP synthetase. In addition to the polymerase chain reaction described herein, preparation of such DNA sequences is also possible by other amplification techniques as well as known synthetic procedures.

A DNA sequence coding for human GMP synthetase can be cloned into a variety of expression vectors. The expression vectors include, for example, plasmids, bacteriophages and cosmids. The particular vector chosen should be compatible with the contemplated host cell, whether a bacterium such as, for example, *E. coli*, or yeast or other cell. A plasmid should have the proper origin of replication for the particular host cell to be employed and suitable restriction sites that allow the ligation of foreign DNA sequences. Furthermore, the plasmid should impart to the transformed cell a phenotypic property that will enable the transformed cells expressing the enzyme to be readily identified from cells that do not undergo transformation. Similar considerations apply to nonplasmid vectors. Numerous expression vectors with a variety of properties are available from commercial suppliers.

The DNA encoding the desired human GMP synthetase, whether in fused or mature form, and whether or not containing a signal sequence to permit secretion, is ligated into an expression vector suitable for any convenient host. Both eukaryotic and prokaryotic host cells are presently used in forming recombinant proteins. By way of illustration and not limitation, eukaryotic systems include human fibroblast HeLa cells and Jurkat T-cells and prokaryotic systems include *E. coli*.

The expressed enzyme is then isolated from lysed cells or from culture medium and purified to the extent needed. Purification is carried out by methods known to the art, including, but not limited to, salt fractionation, ion exchange chromatography, hydrophobic chromatography, gel filtration chromatography, affinity chromatography, isoelectric focusing and centrifugation.

The recombinant human GMP synthetase contemplated by this invention includes all functionally equivalent enzymes obtained by expressing in a host cell a DNA sequence encoding for human GMP synthetase or a fragment thereof, as well as functionally equivalent sequences coding for human biologically active GMP synthetase.

In a preferred embodiment of this invention as described in more detail in Example 4, a DNA coding sequence for human GMP synthetase is subcloned into a baculovirus transfer vector. Insect cells are co-transfected with the transfer plasmid and baculovirus virion DNA. A few days later, when polyhedra are evident in the culture, the culture fluid is harvested and several clones of the recombinant virus plaque are purified. Expression levels of GMP synthetase of each of the recombinant viruses are determined by infecting insect cells and performing enzyme assays on the lysates of the infected cells. One of the clones with a high level of expression is selected for large scale production of the enzyme, wherein insect cells growing in serum free culture fluid are infected with the recombinant baculovirus obtained above. Sometime later the cells are harvested by centrifugation. The cells are suspended in hypotonic buffer and mechanically disrupted. Following clarification by centrifugation, the soluble proteins are fractionated by ammonium sulfate precipitation. The GMP synthetase containing fraction is desalted and the GMP synthetase is purified by sequential anion-exchange and hydrophobic interaction chromatography. A final purification using high resolution anionexchange chromatography results in a purified preparation of GMP synthetase. The purified recombinant human GMP synthetase is a single band on SDS gel electrophoresis as visualized by Coomassie blue staining and has a specific activity of 3.0 $\mu$mol AMP produced/min/mg or greater, often in the range 3.0 to 4.4 $\mu$mol AMP produced/min/mg, when measured by the spectrophotometric-coupled Spector assay referenced earlier.

Assays for inhibitors of human GMP synthetase

The present invention also relates to assays using purified human GMP synthetase to screen for and identify inhibitors of human GMP synthetase. The assay is a method comprising contacting a medium containing the suspected inhibitor with purified human GMP synthetase and measuring the activity of the human GMP synthetase. The medium can be an extract of biological origin, such as, for example, a plant, animal, or microbial cell extract, or alternatively, it may be a substantially pure compound of synthetic origin, or a mixture of compounds thereof.

Enzyme activity can be measured by methods such as direct measurement of the products of the enzymatic reaction or by coupling the formation of the reaction product to the reaction of other detectable species. For example, in one method for determining enzyme activity the formation of AMP and/or GMP is measured by coupling their formation to the oxidation of NADH as mediated via AMP kinase and/or GMP kinase, pyruvate kinase, and lactate dehydrogenase. The oxidation can be monitored spectrophotometrically at 340 nm. In another method for measuring the enzyme activity, radiolabeled XMP or ATP is used as substrate and the formation of radioactive GMP or AMP is measured directly after separation of substrates and products by chromatographic methods such as thin layer chromatography or high pressure liquid chromatography.

Compounds are identified based on their ability to inhibit the activity of the purified human GMP synthetase disclosed herein. The assay is used to identify compounds having an $IC_{50}$ of less than 25 $\mu$M, preferably, less than 20 $\mu$M, more preferably, less than 10 $\mu$M. The preferred inhibitors have an $IC_{50}$ greater than 0 and less than 5 $\mu$M. Usually, the present inhibitors have an $IC_{50}$ of less than 5 $\mu$M, preferably less than 1 $\mu$M, generally 0.01 to 5 $\mu$M, more preferably 0.1 to 1$\mu$M. The inhibitors are used in a method for inhibiting human GMP synthetase activity by administering an effective amount of the inhibitor having an $IC_{50}$ of 5 $\mu$M or less. The effective amount is generally that amount that results in greater than 50% decrease in human GMP synthetase activity, preferably, greater than 70% decrease in human GMP synthetase activity, more preferably, greater than 90% decrease in human GMP synthetase activity.

Antibodies against human GMP synthetase

The present invention also relates to antibodies, both polyclonal and monoclonal, against human GMP synthetase. Methods of preparing polyclonal antibodies are well known to the art. For example, an immunogenic conjugate comprising the human GMP synthetase or a fragment thereof, optionally linked if necessary to a carrier protein, is used to immunize a selected mammal (e.g. mouse, rabbit, goat etc.). Serum from the immunized mammal is collected and treated according to known procedures to separate the immunoglobulin fraction. In one approach in the present invention, the human GMP synthetase is expressed as a fusion transfer protein, such as, for example, glutathione transferase fusion protein, which is used to immunize rabbits according to a conventional procedure.

Monoclonal antibodies are prepared by standard hybridoma cell technology based on that reported by Kohler and Milstein in *Nature* 256 (1975) 495–497. Briefly, spleen cells are obtained from a host animal immunized with human GMP synthetase protein or a fragment thereof, optionally linked to a carrier if necessary. Hybrid cells are formed by fusing these spleen cells with an appropriate myeloma cell line and cultured. The antibodies produced by the hybrid cells are screened for their ability to bind to purified human GMP synthetase. A number of screening techniques well known in the art, such as, for example, forward or reverse enzyme-linked immunosorbent assay (ELISA) screening methods may be employed. The hybrid cells producing such antibodies are then subjected to recloning and high dilution conditions in order to select a hybrid cell that secretes a homogeneous population of antibodies specific to human GMP synthetase. The antibodies of this invention find use in the detection of human GMP synthetase.

The antibodies of this invention can be conjugated to a reporter molecule by techniques well known in the art. Typically the reporter molecule contains a functional group suitable for attachment of the reporter group to the antibody. The functional groups suitable for attaching the reporter group are usually activated esters or alkylating agents which react with nucleophilic groups such as, for example, amino, hydroxyl or thiol groups on the antibody. Details of these and related techniques for attaching reporter groups to proteins are described in reviews such as, for example, *Enzyme-Immunoassay* by E. T. Maggio, published by the CRC Press, Boca Raton, Fla., 1980.

Generation of Nucleic Acid Probe

Purified human GMP synthetase is subjected to peptide digestion, using, for example, trypsin, pepsin, or other proteases and the like, and the peptides are resolved by chromatographic techniques such as, for example, reverse phase high pressure liquid chromatography. The peptides are sequenced. Degenerate oligonucleotides are synthesized corresponding to the derived amino acid sequences of the above peptides. Oligonucleotides are synthesized in both the sense and antisense directions for each peptide and are used as primers in an amplification by the polymerase chain reaction. Since the location of the peptides in the protein sequence is unknown, each oligonucleotide is used with another as primers. A template for the PCR reaction is constructed by generating the cDNA complementary to RNA, such as polyadenylated RNA, from a human cell line expressing GMP synthetase. This is accomplished by extracting the total cellular RNA from the cell line of interest, separating the RNA fraction of interest by column chromatography using the appropriate column substrate, such as, for example, in the case of polyadenylated RNA, an oligo-dT cellulose column, and treating it with reverse transcriptase. A DNA amplification reaction is carried out by repeated primer initiated strand extension and fragments are generated and isolated by appropriate techniques. Polynucleotide probes are prepared by conjugation of reporter molecules to fragments isolated as above.

Identification of DNA sequence encoding for human GMP synthetase

The fragments obtained above are used to screen a cDNA library prepared by using RNA from human cells with a suitable cDNA cloning vector. A wide variety of cloning vectors are available, including lambda vectors and phagemid vectors. Second generation "Okayama-Berg" vectors are also available for efficient cDNA cloning and subsequent expression in mammalian systems. In one such instance using polyadenylated RNA, a number of positive clones are isolated of which the four longest are overlapping. The longest sequence, GMPS.6 (SEQ ID NO: 1), is shown in FIG. 1 and was approximately 2.2 kb. In FIG. 1, amino acid residues are represented in single-letter code. Lines and numbers in parentheses mark the position of sequences corresponding to the tryptic peptides determined from the purified native enzyme. Boxes mark the position of sequences corresponding to the oligonucleotide primers. Nucleotide residue 1 represents the start site of translation.

Sequence analysis of GMPS.6 (SEQ ID NO: 1) reveals an open reading frame of 2079 base pairs (FIG. 1). This open reading frame yields a protein of 693 amino acid residues and a predicted molecular weight of 76,725. This predicted size is in good agreement with the 75 kDA size of the purified human GMP synthetase from natural sources obtained above. The sequences of all nine tryptic peptides are contained within the predicted protein sequence and are shown in Table 2 in Example 2.

Expression of recombinant human GMP synthetase

One embodiment of the invention is exemplified by a recombinant protein prepared by subcloning the cDNA sequence spanning bases 1 to 2090 of GMPS.6 (SEQ ID NO: 1) into the NcoI/Pst I cloning site of the prokaryotic expression vector, pTRC.99A (Pharmacia) which contains an ampicillin resistance marker and the trc promoter that is inducible by IPTG. This plasmid is designated NF.6 (NF designates "no fusion") and contains the entire open reading frame and all of the 3'-untranslated sequence, but none of the 5'-untranslated sequence. A host cell is transfected with the NF.6 plasmid and cultured to express the recombinant protein. Purification of the recombinant protein yields a product of greater than 95% of purity as determined by SDS gel electrophoresis and Coomassie blue staining. The recombinant enzyme of this embodiment has the identical kinetic and biochemical properties as the purified human enzyme described previously.

Functional expression of human GMP synthetase in this fashion is further verified by testing for complementation of guanosine requirement in AT2465 *E.coli* transfected cells which do not grow in absence of guanosine. A second expression vector is constructed as described above except that two stop codons are inserted into the ligated oligonucleotide 39 base pairs downstream from the start site of translation. This expression vector is designated ES.6 (ES abbreviates "early stop") and it coded for a truncated protein, as expected. Both ES.6 and NF.6 are transfected into AT2465 *E. coli*, and the cells are allowed to grow on minimal medium plates containing ampicillin and IPTG with or without guanosine. As shown in FIG. 2, cells that are not transfected do not produce colonies on either plate due to the absence of ampicillin resistance in the parental AT2465 cells. Cells that are transfected with either NF.6 or ES.6 produce colonies in the presence of guanosine. Only cells transfected with NF.6 form colonies in the absence of guanosine. This result shows that GMPS.6 (SEQ ID NO: 1) contains a cDNA that can complement a host *E. coli* that was deficient in GMP synthetase. When this cDNA is mutated in ES.6 by the insertion of stop codons, it can no longer complement growth in the absence of guanosine. These results show complementation by the transfected human DNA.

The transfected cells also show the presence of GMP synthetase enzyme activity. Single colonies are selected from plates without guanosine (NF.6 transfected cells) or with guanosine (ES.6 transfected cells). As shown in FIG. 2, GMP synthetase activity is present in NF.6 transfected cells and absent in ES.6 transfected cells. Furthermore, the activity is induced by the presence of IPTG. There is no detectable GMP synthetase activity in untransfected cells. These findings confirm the complementation results and demonstrate the cloning of a cDNA encoding a functional human GMP synthetase.

EXAMPLES

Materials

Restriction endonucleases and all enzymes used for plasmid construction were purchased from New England Biolabs (Beverly, Mass.); oligo (dT)-cellulose from Pharmacia LKB (Uppsala, Sweden); Taq DNA polymerase from Perkin Elmer Cetus (Norwalk,Conn.); [$\alpha$-$^{32}$P]dCTP from Amersham (Arlington Heights, Ill.); [$\alpha$-$^{32}$P]UTP from Du Pont NEN (Boston, Mass.). All other chemicals were purchased from Sigma (St. Louis, Mo.).

Cells and Media

A3.01 cells were obtained from Dr. Thomas Folks (National Institute of Health, Bethesda, Md. Folks, T., Benn, S., Rabson, A., Theodore, T., Hoggan, M. D., Martin, M., Lightfoote, M., and Sell, K. (1985) *Proc. Natl. Acad. Sci. USA* 82, 4539–4543). The A3.01 cells were cultured in RPMI 1640 media containing 5% fetal bovine serum and 10 μg/ml gentamicin (HyClone, Logan, Utah). CEM, HL60, U937 and WI38 cells were purchased from American Type Culture Collection (Rockville, Md.); Jurkat and UC cells were from Dr. Jeffrey Northrop (Stanford University Medical Center, Stanford, Calif.); VB and HFF cells were provided by the cell culture facility at Syntex Corporation (Palo Alto, Calif.). Normal peripheral T lymphocytes were isolated from a healthy donor according to an approved protocol and purified as described by Eugui, E. M., and Almquist, S. J. (1990) *Proc. Natl. Acad. Sci. USA* 87, 1305–1309.

The bacterial hosts, SURE and XL1-Blue, used in library amplification and screening, were provided by Stratagene (La Jolla, Calif.). The AT2465 strain of *E. coli* was obtained from the *E. Coli* Genetic Stock Center (Yale University, New Haven, Conn.). The AT2465 cells have the following chromosomal markers: thi-1, guaA21, relA1, λ and spoT1. AT2465 cells do not grow in minimal media in the absence of guanosine and thiamin (Taylor, A. L., and Trotter, C. D. (1967) *Bacteriol. Rev.* 31, 332–353 and references therein).

EXAMPLE 1

Purification of Naturally Occurring Human GMP Synthetase

A particularly preferred method of purification of naturally occurring human GMP synthetase from A3.01 cells is described below.

Step 1: Homogenization. In a typical purification, A3.01 cells were cultured in RAMI 1640 media containing 5% fetal bovine serum and 10 μg/ml gentamicin (Hyclone, Logan, Utah). The cells were lysed in 15 ml of buffer A (20 mM Tris.HCl, pH 7.6, 0.1 mM DTT, 0.5 mM EDTA, 10% glycerol) by the use of a glass teflon homogenizer. The homogenate was centrifuged at 15,000×g for 20 min and the pellet was discarded. Purification was carried out with the supernatant (cytosol).

Step 2: Ammonium Sulfate Fractionation. Ammonium sulfate was added to the cytosol fraction obtained above until 35% saturation and the precipitated proteins were removed by centrifugation at 20,000×g for 20 min and discarded. The proteins in the supernatant were precipitated with further addition of ammonium sulfate (60% saturation). These precipitated proteins, which include GMP synthetase, were recovered by centrifugation as above. The protein pellet was dissolved in 12 ml buffer A. Ammonium sulfate was removed from the protein solution by gel filtration chromatography on PD-10 columns (Pharmacia).

Step 3: DEAE-Cellulose Chromatography. The desalted protein fraction obtained above was applied to a 1.5×7.3 cm column of DEAE-cellulose (Whatman) equilibrated in buffer A. The enzyme was eluted with a 60-ml gradient of 0 to 0.5M sodium chloride in buffer A. The fractions containing GMP synthetase activity were pooled.

Step 4: Phenyl-5PW Chromatography. The DEAE cellulose pool obtained above was diluted with an equal volume of 0.2M potassium phosphate, pH 7.0. 1.7M ammonium sulfate, 20% glycerol. The protein sample was applied to a 8 mm×7.5 cm column of Phenyl-5PW (TosoHaas, Montgomeryville, Pa.) equilibrated in buffer B (0.1M potassium phosphate, pH 7.0, 1.7M ammonium sulfate, 10% glycerol). GMP synthetase was eluted with a 40-ml gradient of 1.7 to 0M ammonium sulfate in buffer B and the fractions containing active enzyme were pooled.

Step 5: Mono-Q Chromatography. The Phenyl-5PW pool obtained above was desalted as above and applied to a Mono Q HR 5/5 column (Pharmacia) equilibrated with buffer C (20 mM Tris. HCl, pH 8.0, 0.1 mM DTT, 20% glycerol). GMP synthetase was eluted with a 30-ml gradient of 0–0.3M sodium chloride in buffer C. The GMP synthetase fractions that contained a single Coomassie blue-staining band at 75 kDa were pooled. This material is purified human GMP synthetase.

A purification table from a representative purification for the various steps of the process is shown in Table 1 below. Enzyme activity was determined by using the spectrophotometric-coupled assay of Spector performed exactly as described (T. Spector; *Methods Enzymology*, 51, 219–224, (1978)), incorporated herein by reference. This assay measured the rate of AMP production by GMP synthetase, and the level of AMP is measured through the activity of three auxiliary enzymes. When crude enzyme samples such as those in steps 1 to 3 of the purification were examined, this assay method measured a high rate of AMP formation even in the absence of the GMP synthetase substrate, XMP. This rate is referred to as background rate. The GMP synthetase activity shown in Table 1 below was the rate of AMP formation in the presence of all the substrates subtracted by the background rate when XMP is omitted. The GMP synthetase activity determined by this assay was the same as the activity determined by measuring radioactive GMP formation as described below in Example 3.

TABLE 1

| sample | total protein (mg) | total actvity (μmol AMP/min) | specific activity (μmol AMP/min-mg) | fold purified |
|---|---|---|---|---|
| cytosol | 2478.55 | 7.42 | 0.0030 | 1 |
| 35–60% AS precipitate | 1095.46 | 10.24 | 0.0094 | 3 |
| DEAE-cellulose pool | 46.64 | 3.25 | 0.0670 | 23 |
| Phenyl-5PW pool | 3.95 | 1.59 | 0.4038 | 135 |
| Mono Q pool | 0.17 | 0.47 | 3.0 | 936 |

Figure 3:
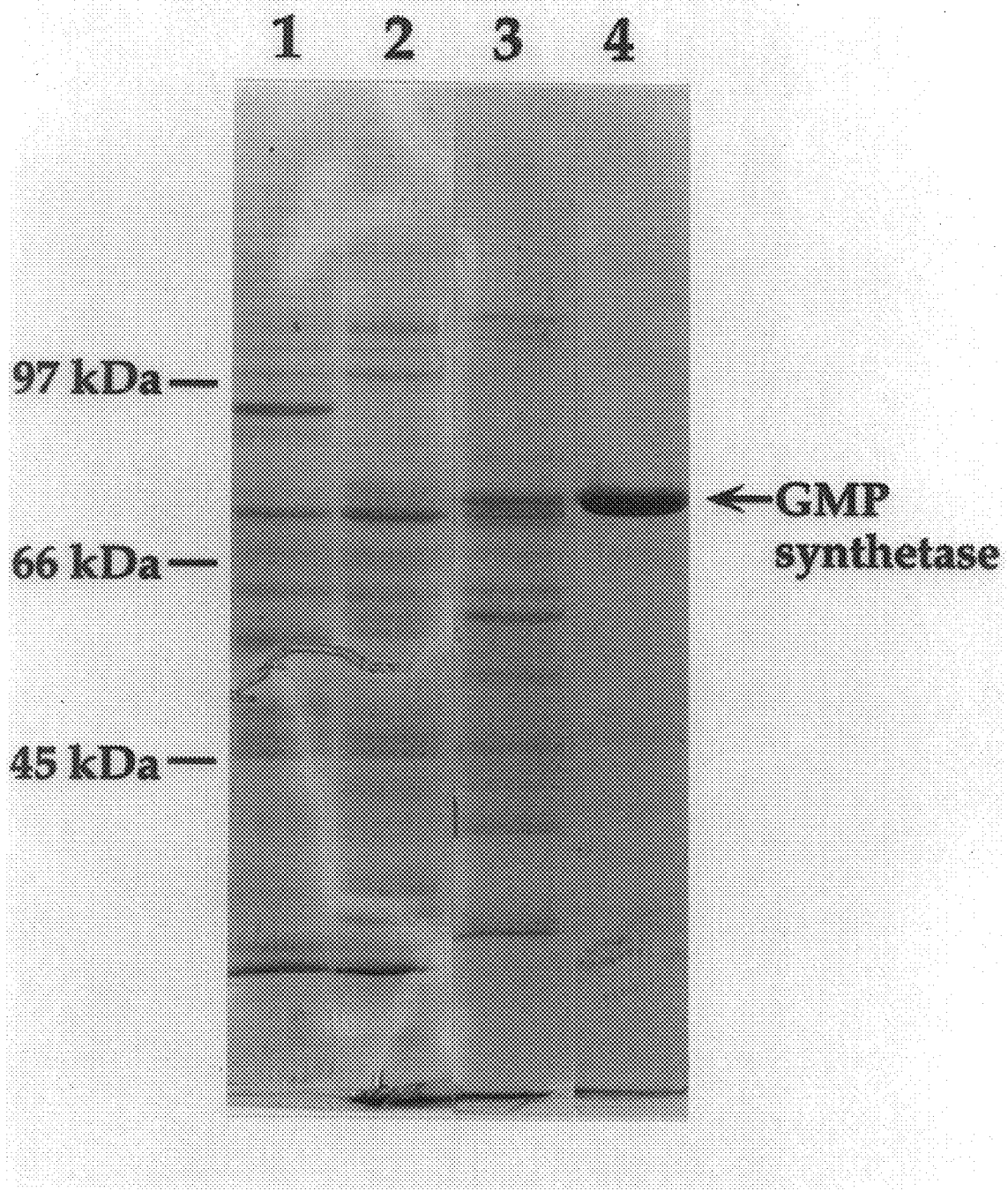
FIG. 3. Purification of GMP synthetase from A3.01 cells. Samples from each step of the purification were subjected to SDS polyacrylamide gel electrophoresis and stained with Coomassie blue. The purification step and amount of protein loaded in each lane are as follows: lanes 1. 35–60% ammonium sulfate precipitate, 6 $\mu$g; 2. DEAE-cellulose pool, 2.5 $\mu$g; 3. Phenyl-5PW pool, 3 $\mu$g; 4. Mono Q pool, 3 $\mu$g.

FIG. 3 shows the SDS polyacrylamide gel electrophoresis of each step in the purification. Samples from each step of the purification were subjected to SDS polyacrylamide gel electrophoresis and stained with Coomassie blue. The purification step and amount of protein loaded in each lane are as follows: lanes 1. 35–60% ammonium sulfate precipitate, 6 μg; 2. DEAE-cellulose pool, 2.5 μg; 3. Phenyl-5PW pool, 3

μg; 4. Mono Q pool, 3 μg. The purified human GMP synthetase was essentially one band after the final purification step.

The above purification was repeated on several occasions and samples of human GMP synthetase with specific activities in the range of 2.5–4.0 μmol AMP produced/min/mg were routinely obtained.

EXAMPLE 2
Generation of Nucleic Acid Probes and Identification of the Gene for Human GMP Synthetase GMP synthetase from A3.01 cells was purified to homogeneity as described above and digested with trypsin. Nine tryptic peptides were resolved by reverse-phase high-pressure liquid chromatography (RP-HPLC) and subjected to sequence analysis by Edman degradation using an ABI470A sequencer (Applied Biosystems, Foster City, Calif.). The sequences of the nine peptides are shown in Table 2 below. The sequences are represented by the standard one-letter code. The letter "X" indicates that no amino acid can be assigned from the corresponding cycle of Edman degradation.

TABLE 2

| Peptide | Sequence |
| --- | --- |
| 1 | NIVAGIANESK (SEQ ID NO: 2) |
| 2 | ALNQEQVIAVXIDNGFM (SEQ ID NO: 3) |
| 3 | VINAAHSFYNGTXXLPISDED (SEQ ID NO: 4) |
| 4 | IIGDTFV (SEQ ID NO: 5) |
| 5 | ANEVIGXMNLK (SEQ ID NO: 6) |
| 6 | VIEPLKDFIKDEVR (SEQ ID NO: 7) |
| 7 | PFPGPGLAI (SEQ ID NO: 8) |
| 8 | FITSDFMTGIPATPGNEIXV (SEQ ID NO: 9) |
| 9 | IMYDLTSKPPGTTE (SEQ ID NO: 10) |

Figure 4:
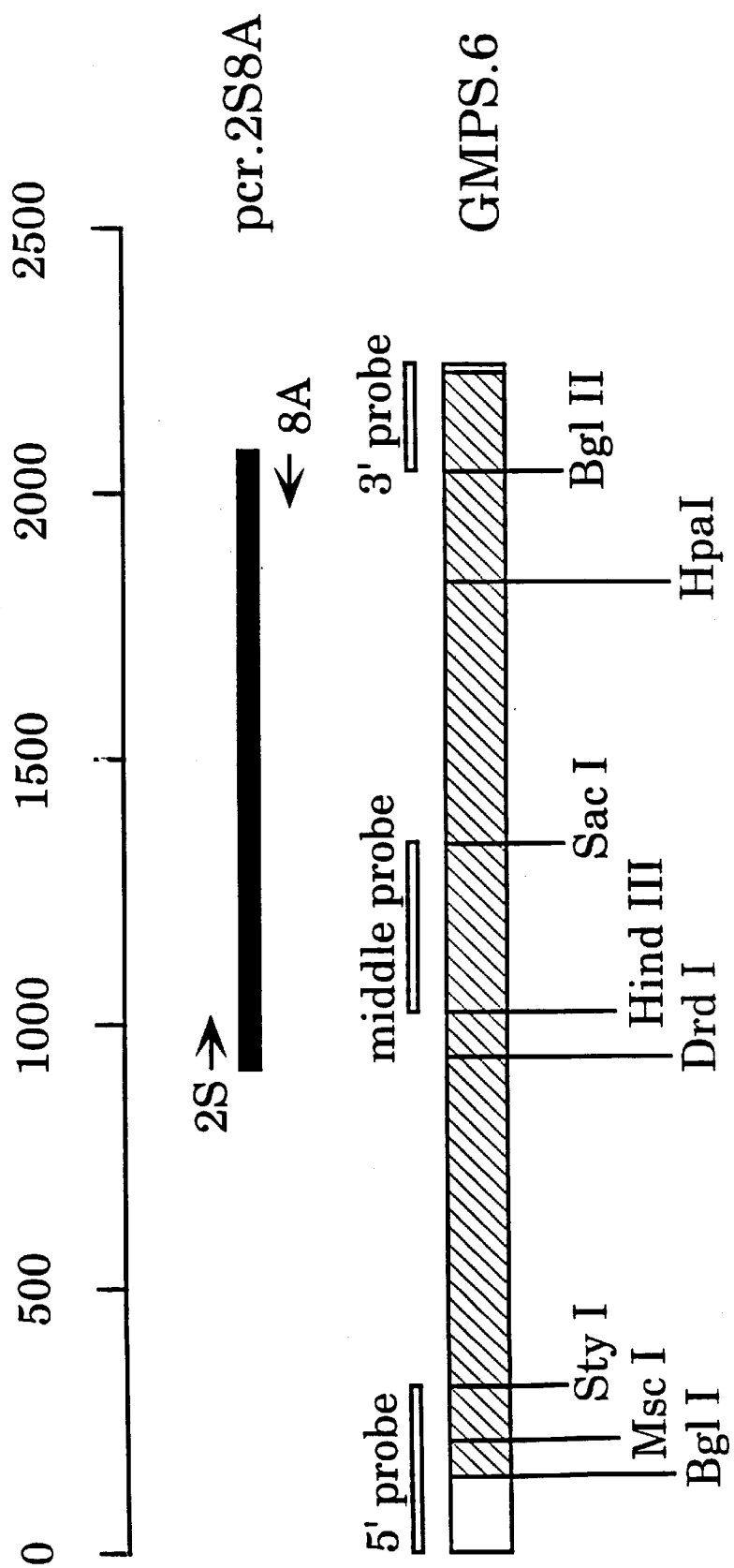
FIG. 4. Restriction map of GMPS.6 (SEQ ID NO: 1) and probes.
The region of hatched bars indicates the position of the longest open reading frame. The scale gives length in base pairs. The black bar marks the length and position of the PCR fragment pcr.2S8A. The open bars mark the length and position of the CDNA fragments used as probes in northern and Southern hybridization analysis. The small arrows mark the position and direction of oligonucleotide primers 2S and 8A in the 5' to 3' orientation.

Based on the peptide sequences, degenerate oligonucleotides were synthesized using the phosphoramidite method with a Cyclone Plus DNA Synthesizer (MilliGen/Biosearch, Burlington, Mass.). Oligonucleotides were synthesized in both the sense and antisense orientations for each peptide and used as primers in polymerase chain reactions (PCR). To generate the template, DNA complementary to A3.01 polyadenylated RNA was prepared using avian reverse transcriptase (Life Sciences) using the methods disclosed by Sambrook, J., Fritsch, E. F., and Maniatis, T. (1989) *Molecular Cloning: A Laboratory Manual*, 2nd Ed., Cold Spring Harbor Laboratory, Cold Spring Harbor, N.Y. DNA amplification was performed using *Thermus aquaticus* (Taq) polymerase in a Perkin-Elmer/Cetus DNA thermal cycler using the methods disclosed in Heller, R. A., Song, K., Onasch, M. A., Fischer, W. H., Chang, D., and Ringold, G. M. (1990), *Proc. Natl. Acad. Sci. USA*, 87, 6151–6155. A specific fragment of approximately 1-kb in length was generated only when oligonucleotides $2S^2$ and $8A^2$ (corresponding to tryptic peptides 2 and 8) were used as primers (FIGS. 1 and 4). To confirm the identity of this fragment, it was subcloned into pCR.1000 (Invitrogen, San Diego, Calif.). From partial sequence analysis, the sequences corresponding to 2S and 8A at the 5' ends of the forward and reverse strands respectively, as well as the sequence of oligonucleotide 3S2 (corresponds to peptide 3) near the 5' end of the forward strand (see FIGS. 1 and 4) were detected. This PCR fragment (pcr.2S8A) was used to screen an A3.01 cDNA library. Based on subsequent sequence analysis of GMPS.6, (SEQ ID NO: 1)the sequence of pcr.2S8A corresponds to the sequence within FIG. 1 starting from residue 781 and ending at residue 1952.

Screening of cDNA Library and Sequencing of Positive Clones

A cDNA library, prepared by Stratagene (La Jolla, Calif.), was constructed in the Lambda-ZAP II vector system using polyadenylated RNA from A3.01 cells. To obtain polyadenylated RNA, total cellular RNA was isolated according to the method of Chirgwin et al (Chirgwin, J. M., Przybyla, A. E., MacDonald, R. J., and Rutter, W. J. (1979) *Biochemistry* 18, 5294–5299) and polyadenylated RNA was then obtained using oligo(dT) -cellulose as described by Aviv et al (Aviv, H., and Leder, P. (1972) *Proc. Natl. Acad. Sci. USA* 69, 1408–1412). The resulting cDNA library prepared by Stratagene yielded $9.3 \times 10^6$ primary plaques with the host bacterial strain SURE (Stratagene, La Jolla, Calif.). Amplification was performed on $1 \times 10^6$ plaque forming units (pfu).

The amplified library was screened according to a standard procedure provided by Stratagene. The PCR fragment pcr.2S8A was radiolabeled by random-hexamer priming and it was used as a probe. A total of $0.9 \times 10^6$ pfu were screened. After three rounds of screening, eight positive phagemids were excised and rescued by R407 helper phage (Stratagene). Doubled stranded pBluescript (SK) plasmids were isolated, and four of the longest clones were analyzed further by restriction mapping and found to be overlapping.

The cDNA inserts of the four positive clones were sequenced by the method of Sanger using fluorescent dye-labeled terminators with a 373A DNA Sequencer (Applied Biosystems). Partial sequence analysis confirmed that the four clones were overlapping. The complete sequence of both strands of the insert of clone 6 (GMPS.6, SEQ ID NO: 1) was determined and is shown in FIG. 1. Sequence analysis of GMPS.6 revealed an open reading frame of 2079 base pairs (FIG. 1). The first ATG was found at 142 bases downstream from the 5' end and a stop codon TAA was found 11 bases upstream from the 3' end. No poly(A) tail was found on any of the clones. The open reading frame yielded a protein of 693 amino acid residues with a predicted molecular weight of 76,725. The derived amino acid sequence (SEQ ID NO: 11) of human GMP synthetase is shown in FIG. 1. The predicted size of the enzyme was in good agreement with the 75-kDa size indicated by polyacrylamide gel electrophoresis of the purified A3.01 human GMP synthetase described in Example 1. The sequences corresponding to the nine tryptic peptides were located within the predicted peptide sequence.

EXAMPLE 3
Construction of Expression Plasmids and Complementation in AT2465 Cells The insert of GMPS.6 was excised from the pBluescript plasmids obtained above and cloned into the Nco I/Pst I cloning site of the prokaryotic expression vector, pTRC99A (Pharmacia), to yield vector TRC.6. Using TRC.6, two expression vectors, NF.6 and ES.6, were constructed to remove the 5'-untranslated sequence of the cDNA. A 201-bp fragment was removed from the 5' end of the TRC.6 by digestion with Nco I and Msc I, and replaced with a 60 base pair-oligonucleotide that had the identical sequence of residues −1 to 59 except for a G to C change at residue −1 (see FIG. 1, residue 1 represents the start site of translation). This base change converted the Bgl I site at the start site of translation to an Nco I site. The 60 base pair-oligonucleotide which has the sequence 5'-CATGGC●●●● was directly ligated into the Nco I/Msc I cut vector, and this expression vector was designated NF.6 (NF abbreviates "no fusion"). A second expression vector ES.6 was constructed in the same manner except that two stop codons were inserted in the ligated oligonucleotide 39 base pairs downstream from the start site of translation (ES abbreviates "early stop"). With reference to FIG. 1, the nucleotide sequence from residues 40 to 45 was changed from●●●●GGAGGA●●●● to ●●●●TGATAA●●●●.

To test for complementation of the guanosine requirement, AT2465 cells that were transfected with NF.6 or ES.6 were spread on M9 minimal media plates with or without guanosine (100 μ/ml). All plates were supplemented with 0.4% glucose, 0.2% casamino acids, 20 μg/ml IPTG and 100 μg/ml of: thiamin, glutamine, histidine, arginine, inosine, biotin, 2'-deoxyuridine and ampicillin. Colony formation was examined after 16–48 h of growth.

Cells that were not transfected did not produce colonies on either plate due to the absence of ampicillin resistance in the parental AT2465 cells (FIG. 2). Cells that were transfected with either NF.6 or ES.6 produced colonies in the presence of guanosine. Only cells transfected with NF.6 formed colonies in the absence of guanosine. This result showed that GMPS.6 contained a cDNA that could complement a host E. coli that was deficient in GMP synthetase. When this cDNA was mutated in ES.6 by the insertion of stop codons, it could no longer complement growth in the absence of guanosine. These data show complementation by the transfected human DNA.

To determine GMP synthetase activity, single colonies were selected and inoculated in LB media containing 100 μ/g/ml ampicillin. Cultures were allowed to grow to mid-log phase and then IPTG was added to a final concentration of 20 μg/ml. Cells were harvested 3 h after the addition of IPTG.

Determination of Enzyme Activity in Transfected E. Coli Cells

Cells were resuspended in lysis buffer (20 mM Tris-HCl, pH 7.6, 0.5 mM DTT, 0.2 mg/ml lysozyme, 2 mM PMSF, 0.5, mM EDTA, and 10% glycerol) and lysed at 37° C. for 10 min. Genomic DNA was sheared by passing the lysate through a 27 gauge needle three to four times. The cytosolic fraction was separated from the membrane fraction by centrifugation at 15,000×g for 15 min. GMP synthetase activity in the cytosol was determined by measuring the formation of [8-$^{14}$C]GMP from [8-$^{14}$C]XMP (50 mCi/mmol, Moravek, Brea, Calif.). The assay mixture contained 75 mM Tris-HCl, pH 7.8, 10 mM MgCl$_2$, 2 mM ATP, 1 mM [$^{14}$C]XMP (10 mCi/mmol), 5 mM glutamine and 50 mM DTT. Typically, 5 μl of cytosol was added to 25 μl of assay mix, and the reaction was allowed to proceed at 40° C. for 15 min. The reaction was stopped by the addition of 6 μl of quench solution, which contained 250 mM EDTA and 62.5 mM each of GMP and XMP as carriers. GMP and XMP were separated by thin layer chromatography as described (Boritzki, T. J., Jackson, R. C., Morris, H. P., and Weber, G.; (1981) Biochim. Biophys. Acta, 658, 102–110). Briefly, the quenched reaction mixtures (10 μl) were streaked onto 2.5 cm×20 cm strips of polyethyleneimine cellulose plates (Macherey-Nagel, Germany). The strips were developed in 2 M formic acid. The position of GMP was visualized by ultraviolet light and marked. The GMP band was excised, and the amount of [$^{14}$C]GMP was determined by liquid scintillation counting. Protein concentration was determined by Bradford analysis (Bio-Rad).

The results shown in FIG. 2 demonstrate that GMP synthetase activity was present in NF.6 transfected cells and absent in ES.6 transfected cells. Furthermore, the activity was induced by the presence of IPTG. There was no detectable GMP synthetase activity in untransfected cells. These findings confirm the complementation results and demonstrate that the cloning of a cDNA encoding a functional human GMP synthetase.

EXAMPLE 4

Expression Production and Purification of Recombinant Human GMP Synthetase

Lipofection:

A lipid solution consisting of lipofectin (0.067 mg/ml) in Hepes Buffered Saline (HBS), (20 mM Hepes, 150 mM NaCl, pH 7.4) and a DNA solution containing 0.33 ug Autographa californica Nuclear Polyhedrosis Virus DNA (BaculoGold®, PharMingen, San Diego, Calif.) and 3.3 ug transplacement plasmid (pSYN-GMPS) DNA were prepared.

The transplacement plasmid, pSYN-GMPS, was prepared as follows. The coding region of the GMP synthetase cDNA was excised from NF.6 and cloned into the baculovirus expression vector pSynXIV VI$^+$X3 (Wang, X., Ooi, B. G., and Miller, L. K. (1991) Gene 100, 131–137) to yield pSyn.GMPS. The vector pSynXIV VI$^+$X3 was linearized at the EcoRI site in the multiple cloning region downstream from the promoter, and the 3'-recessed sequences were filled in using Klenow fragment as described in Sambrook, J., Fritsch, E. F., and Maniatis, T.(1989) Molecular Cloning: A Laboratory Manual, 2nd Ed., Cold Spring Harbor Laboratory, Cold Spring Harbor, N.Y. The blunt-ended vector was digested with PstI which removed one blunt end. NF.6 was linearized with NcoI which cleaved NF.6 at the start site of translation. Blunt ends were created as described above and the vector was cut with PstI to release the coding region insert. The insert, which was blunted at the 5'-end and cleaved at the 3'-end with PstI, was cloned into the blunt/PstI cloning site of the pSynXIV VI$^+$X3 vector to yield the pSYN-GMPS expression vector.

Plastic flasks (Costar, tissue culture, 25 cm$^2$ surface area) were seeded with 3×10$^6$ Spodotera frugiperda (Sf-9) cells (ATCC, Rockville, Md.) that had been adapted to grow in suspension in ExCell-400 medium (JRH Scientific). After 1 hour the cells which had attached to the flask were washed with HBS and three milliliters of lipofection solution consisting of 1 part lipid solution and 1 part DNA solution were added to the monolayer. After 40 minutes at 28° C., three milliliters of ExCell-400 medium supplemented with 10% fetal calf serum and gentamicin (50 ug/ml) were added to the lipofection solution in the flask. Thirty minutes later the lipofection solution was decanted and replaced with fresh ExCell-400 medium supplemented with 2.5% fetal calf serum. Five days later, the culture fluid was collected (5 day harvest) and centrifuged at 2000 rpm for 15 minutes. Fresh Ex-Cell 400 medium supplemented with 2.5% FCS was added to the flask and a second harvest is taken 2 days later (7 day harvest).

Plaque Purification of Recombinant Baculovirus:

The clarified culture fluid from the transfected cells (either the day 5 or day 7 harvest) was serially diluted for 1×10$^{-1}$ to 1×10$^{-6}$. Six-well plates (Linbro, tissue culture, 9.6 cm$^2$ surface area per well) were inoculated with 2 ml Sf-9 cell suspension (0.6×10$^6$ cells/ml ExCell-400). When the cells attached, 1 hour after seeding, each well was inoculated with 0.5 ml of each dilution of the culture fluid in duplicate. Viral adsorption continued for 1 hour at 28° C. The plates were rocked every 15 minutes to facilitate distribution of the virus particles. The inoculum was then aspirated, and the cell monolayers in each well overlayed with 2 ml of a solution containing 1 part 2× ExCell-400, 1 part 3% melted Sea-Plaque Agarose, and gentamicin (50 ug/ml). The plates were incubated in a humidified environment at 28° C. for 5 days until plaques had developed. A second 2 ml overlay that contained 0.1 mg/ml Neutral Red (GIBCO Labs, Grand Island N.Y.) as well as the components of the first overlay was added to each well. The following day, plaques were readily visible. When observed under a dissecting microscope, polyhedra could be seen at the center of the plaques. Plaques were picked with a P-200 Pippettman® with the volume adjusted to 100 ul and equipped with a sterile tip. Four well separated plaques were picked and dispensed into 0.5 ml fresh ExCell-400 medium. The virus from each plaque was repurified three times.

Preparation of Master Seed Virus:

After the third cycle of plaque purification, virus from a single plaque suspended in 0.5 ml ExCell 400 was inoculated into a well of a 6 well plate containing $1.2 \times 10^6$ cells. After 1 hour adsorption, 1.5 ml ExCell 400 medium was added to each plate. The plates were incubated at 28° C. in a humidified environment for 4–5 days when polyhedra were evident in 70–80% of the cells. The culture fluid from each well was clarified by centrifugation at 1500×g for 10 minutes. Once the culture fluid was titered, a 100 ml Sf-9 cell culture suspended in a 250 ml plastic Erlenmeyer shake flask at a density of $1.2 \times 10^6$ cells/ml was infected with the above virus. The ExCell 400 medium was supplemented with 1% BSA or 5% FCS and 4% feed solution. The feed solution consists of 1.25% glutamine, 2.5% glucose, 12.5× lipid concentrate (GIBCO-BRL, Grand Island, N.Y., cat. # 21900-004), and 12.5× yeastolate ultrafiltrate (GIBCO-BRL, Grand Island, N.Y., cat # 18200-014). The multiplicity of infection was 0.5 plaque forming units per cell. The cells were maintained in suspension by shaking at 140 rpm in a rotary shaker at 28° C. Four days after infection, the culture fluid was harvested by centrifugation at 1500×g for 10 minutes. The supernatant was collected and titered. Aliquots were frozen at −80° C.

Preparation of Working Seed Virus Stock:

An aliquot of master seed virus was thawed and a 100 ml culture of the Sf-9 cells growing in ExCell-400 in a 250 ml plastic Erlenmeyer flask was infected at a MOI of 0.5. The medium was supplemented with either a 1% BSA or 5% FCS and 4% feed solution. The cells were incubated at 28° C. at 140 rpm in a rotary shake flask for four days. The cells were then pelleted and the culture fluid was utilized as working seed passage 1. The virus was titered and stored at 4° C. until needed. In order to increase the amount of virus needed for large scale production of human GMP synthetase working seed passage virus 1 is used to infect fresh Sf-9 cells as described above. The virus from this second round of infection is referred to as working seed passage 2. It is harvested as described above and stored at 4° C. until needed.

Sf-9 cells ($1.2 \times 10^6$/ml) growing in 2 liters of ExCell-400 medium in a 3 liter bioreactor (Applikon, Foster City, Calif.) were infected with working seed passage 1 virus at a multiplicity of infection (MOI) of 0.5. The cells were maintained in suspension by rotation of the impellars at 100–200 rpm. The medium, ExCell-400, was supplemented with 0.1% Pluronic F68, 50 ug/ml gentamicin and antifoam AF Emulsion (JRH Biosciences, Lenexa, Kans.) up to 10 ppm. The culture was also fed 80 ml feed solution at the time of infection. The pH was maintained at 6.3 by titration with 2N NaOH and the dissolved oxygen was maintained at 30% saturation by sparging with air and adjusting the impellar speed. After four days at 28° C., the cells were pelleted by centrifugation and the supernatant was titered and stored at 4° C. until needed.

Production of Human GMP Synthetase:

Production of GMPS was carried out in 10 liters of ExCell-400 supplemented with 1% Pluronic F68. The cells were infected at a density of $1.2 \times 10^6$ cells per ml with working seed passage 2 at an MOI of 0.5. The cells were fed with 400 ml feed solution at the time of infection. The culture was maintained at 27° C. and the pH adjusted to 6.3 with 2N NaOH, and 30% saturation dissolved oxygen for three days. The ExCell-400 medium was supplemented with gentamicin as described above. The cells were then harvested by centrifugation and frozen at −80° C. until needed for purification.

Purification of GMP Synthetase:

Sf-9 cells obtained from above were suspended in lysis buffer (20 mM Tris pH 8.0, 0.5 mM EDTA, 0.5 mM DTT, 10% glycerol, 2 ug/ml leupeptin, 2 ug/ml pepstatin, 2 ug/ml aprotinin). After mixing for 10 minutes, the cells were transferred to a Dounce (type B) homogenizer and the cells disrupted with 20 strokes of the homogenizer. Nuclei and other cell debris were pelleted by centrifugation for 20 minutes at 41,000×g. Ammonium sulfate was added to the supernatant slowly to give a 35% saturation solution. After stirring for 30 minutes, the preparation was subjected to centrifugation (41,000×g, 20 minutes). The pellet was discarded and additional ammonium sulfate added to the supernatant so that the final concentration was 60% of saturation. The mixture was stirred 30 minutes and then subjected to centrifugation (10,000×g, 10 minutes). The pellet was resuspended in an equal volume of lysis buffer and transferred to a 6000–8000 mwco dialysis bag. The suspension is dialyzed against 10 volumes of dialysis buffer for 16 hours.

The dialyzed suspension was then centrifuged at 41,000×g for 20 minutes. The supernatant was filtered through a 0.45 $\mu$m filter and the conductivity was adjusted to less than 3.6 $\mu$MHO with $H_2O$. The preparation was then loaded onto a Q-Sepharose FF column (Pharmacia) at a linear flow rate of 1.4 cm/min. All subsequent operations were at a flow rate of 20 cm/min. Protein elution was monitored continuously at following the optical density of the eluent at 280 nm. The column was then washed with buffer A (20 mM Tris, pH 8, 0.5 mM EDTA, 0.5 mM DTT, 10% glycerol) until optical density at 280 nm returned to baseline. Bound proteins were eluted by running a gradient against buffer B (1M NaCl, 20 mM Tris, pH 8, 0.5 mM EDTA, 0.5 mM DTT, 10% glycerol). The gradient went to 25 buffer B over 50 minutes. Fractions were assayed for GMP synthetase activity and those with appreciable activity were pooled.

Ammonium sulfate was added slowly to the pooled fractions from the Q-Sepharose column (1.94 grams per 10 ml). The solution was then filtered through a 0.8 $\mu$m filter. A Poros PE phenyl ether (PerSeptive Biosystems, Cambridge, Mass.) column was equilibrated against buffer C (20 mM Tris pH 8, 0.5 mM DTT, 10% glycerol, 19.4% ammonium sulfate) at a linear flow rate of 1.7 cm/min.

The protein was then loaded onto the column which was then washed with the equilibration buffer until optical density returned to baseline. This and subsequent operations were at 3.4 cm/min. A 0–60% buffer D (20 mM Tris pH 8, 0.5 mM DTT, 10% glycerol) gradient was run over a 36 minute interval. Fractions were assayed for GMP synthetase activity and those with appreciable activity were pooled. The protein was concentrated to approximately 2 mg/ml using a YM 30 membrane (Amicon)in a stir cell. The protein preparation was mixed with 1 part glycerol and frozen at −80° C. The purified protein had kinetic and biochemical properties identical to those described of the purified human GMP synthetase from A3.01 cells described in Example 1. The specific activity of the enzyme was 4.4 $\mu$mol AMP produced/min/mg.

The above procedure was repeated on several occasions and samples of recombinant human GMP synthetase with specific activities in the range of 3.0–4.4 $\mu$moles AMP produced/min/mg were routinely obtained.

EXAMPLE 5

Assay for Inhibitors of Human GMP Synthetase

The source of enzyme was a baculoviral expressed human GMP synthetase obtained as described above. Alternatively, purified enzyme from A3.01 cells obtained as described in Example 1 was also used. Purified human GMP synthetase enzyme was used in testing. The specific activity of the enzyme used was between 2.5 to 3.0 μmol AMP produced/min/mg. Two procedures were used for assaying enzyme activity in the presence of a suspected inhibitor.

Procedure #1: Spectrophotometric-coupled assay

The formation of AMP was measured by coupling the GMP synthetase reaction to three auxiliary enzymes: these were AMP kinase, pyruvate kinase and lactate dehydrogenase. In addition to the substrates for GMP synthetase, also included in the assay mix were phosphoenol pyruvate (substrate for pyruvate kinase) and NADH (substrate for lactate dehydrogenase). Through the activities of these auxiliary enzymes, the formation of AMP was measured by the eventual oxidation of NADH which was monitored by the decrease of absorbance at 340 nm. This procedure could be automated in a high throughput screen. Because this assay is an indirect assay and an active compound can be inhibiting any or all four enzymes involved in the assay, it is used as a primary screen for quickly identifying potentially active inhibitors.

Procedure #2: Radioactive (direct) assay

In this assay, radiolabeled XMP or ATP was used and the formation of radioactive GMP or AMP was measured directly after separation of substrates and products by thin-layer chromatography. This assay was used to confirm results from the primary screen. Typically, a suspected inhibitor was dissolved and diluted in DMSO and the final DMSO concentration in the assay was 10%.

Assay #1: Spectrophotometric-coupled assay for initial screen
Materials: Stock solutions are prepared and stored frozen until used.

| Reagent | Concentration |
|---|---|
| 1. Tris.HCl, pH 7.8 | 750 mM |
| 2. MgCl$_2$ | 100 mM |
| 3. ATP | 400 μM |
| 4. XMP | 200 μM |
| 5. glutamine | 2000 μM |
| 6. phosphoenolpyruvate | 5 mM |
| 7. NADH | 1.5 mM |
| 8. KCl | 80 mM |
| 9. dithiothreitol | 1 M |
| 10. compound or extract of suspected inhibitor | 0 to 200 μM or 50 μg/ml in DMSO (10% DMSO final) |
| 11. AMP kinase | 1 mg/ml (2000 U/ml) |
| 12. pyruvate kinase | 10 mg/ml (2000 U/ml) |
| 13. lactate dehydrogenase | 10 mg/ml (8500 U/ml) |
| 14. GMP synthetase | 20 μg/ml |

Method
1. Prepared assay mix by mixing 1 ml each of reagents 1–8, 0.5 ml of reagent 9 and 0.1375 ml of distilled H$_2$O. This is solution A.
2. Pipetted 2.764 ml of solution A into a tube and warm to 40° C.
3. Diluted 50 μl of compounds/extracts (reagent 10) into UV-quality disposable cuvettes.
4. Prepared auxiliary enzyme mix by mixing 25 μl of each of reagents 11 and 12, and 12.5 μl of reagent 13.
5. Added 20 μl of auxiliary enzyme mix (from step 4) to 2.764 ml of warm assay mix from step 2.
6. Aliquoted 435 μl of the warm assay/auxiliary enzyme mix from step 5 into the individual cuvettes from step 3 containing the suspected inhibitory compounds or extracts.
7. Started reaction by the addition of 15 μl GMP synthetase to the cuvettes from step 6.

The final concentrations of all assay components are shown below.

| Reagent | Final concentration (in assay) |
|---|---|
| 1. Tris.HCl, pH 7.8 | 75 mM |
| 2. MgCl$_2$ | 10 mM |
| 3. ATP | 40 μM |
| 4. XMP | 20 μM |
| 5. glutamine | 200 μM |
| 6. pyruvate | 0.5 mM |
| 7. NADH | 0.15 mM |
| 8. KCl | 8 mM |
| 9. dithiothreitol | 50 mM |
| 10. compound or extract of suspected inhibitor | 0 to 200 μM or 50 μg/ml in DMSO (10% DMSO final) |
| 11. AMP kinase | 2.5 μg/ml |
| 12. pyruvate kinase | 25 μg/ml |
| 13. lactate dehydrogenase | 1.25 μg/ml |
| 14. GMP synthetase | 0.6 μg/ml |

The assay was run at 40° C., 10 min, 0.5 ml final volume, monitoring continuous change in OD$_{340}$. A negative control was run using 50 μl of DMSO instead of the suspected inhibitory compound or extract.

Assay #2: Radioactive (direct) assay for confirmation screen
Materials:

| Reagent | Concentration |
|---|---|
| 1. Tris.HCl, pH 7.8 | 750 mM |
| 2. MgCl$_2$ | 100 mM |
| 3. ATP | 400 mM |
| 4. XMP | 2.5 mM |
| 5. $^{14}$C-XMP | 1 mM (50 mCi/mmol) |
| 6. glutamine | 2 mM |
| 7. dithiothreitol | 1 M |
| 8. compound or extract of suspected inhibitor | 0 to 200 μM or 500 μg/ml in DMSO |
| 9. GMP synthetase | 2.57 μg/ml |

Method
1. Prepared assay mix by mixing 60 μl each of reagents 1, 2, 3, and 6, 30 μl of reagent 7, 4.8 μl of reagent 5, 2.9 μl of reagent 4, and 122.3 μl of distilled H$_2$O. This is solution A.
2. Warmed assay mix (solution A) to 40° C.
3. Diluted 3 μl of compounds/extracts into 0.4 ml Eppendorf tubes.
4. Aliquoted 20 μl of warm assay mix from step 2 into the individual tubes containing the suspected inhibitors.
5. Started the reaction by the addition of 7 μl of GMP synthetase.
6. Stopped the reaction after 10 minutes with 3 μl 500 mM EDTA.
7. Spiked reaction with 3 μl of standards of GMP and XMP (125 mM each).
8. Streaked 5 μl assay mix (twice, total 10 μl) onto PEI cellulose TLC plates (previously cut into 2.5 cm×20 cm).
9. Chromatographed in 2M formic acid.
10. Visualized GMP band by UV lamp.
11. Excised GMP band and added 4 ml scintillation cocktail (Beckmann Readysafe).
12. Determined $^{14}$C-GMP formation by liquid scintillation counting.

The assay was run at 40° C. for 10 minutes in a final volume of 30 μl. A negative control was run using 3 μl of DMSO instead of the suspected inhibitory compound or extract. Several compounds which inhibited GMP synthetase by 50% or more under these conditions were identified using this screening procedure. The IC$_{50}$ of some of these compounds is shown below.

| Compound | IC$_{50}$ |
|---|---|
| A | 30 μM |
| B | 3 μM |
| C | 0.5 μM |
| D | 7 μM |
| E | 3 μM |
| F | 10 μM |

EXAMPLE 6

Generation of Anti-GMP Synthetase Antibody

An ~300 base pair Hind III/Sac I fragment from the middle of the coding region of clone 6 (GMPS.6) obtained in Example 2 (see FIG. 4) was subcloned into the bacterial expression vector pGEX-2T (Pharmacia) and expressed as a glutathione transferase fusion protein in SURE bacteria. This fusion protein was isolated using a glutathione sepharose column according to Pharmacia instructions. A one liter culture yielded 1.5 mg of protein, which was used to immunize rabbits according to an approved protocol. Rabbit sera were collected and the immunoglobulin fraction was isolated. Purified human GMP synthetase was used in immunoblot analysis to test for the presence of antibodies against human GMP synthetase. In this fashion polyclonal rabbit antibodies were obtained.

Although the foregoing invention has been described in some detail by way of illustration and example for purposes of clarity and understanding, it will be obvious that certain changes and modifications may be practiced within the scope of the appended claims.

What is claimed is:

1. A method for identifying inhibitors of human GMP synthetase, which method comprises exposing a putative inhibitor to purified human GMP synthetase and measuring the activity of the GMP syntethase in the presence of said putative inhibitor, wherein said GMP synthetase has an initial specific activity of at least 2.5 μmoles of AMP produced/min/mg, and inhibition is confirmed by a decrease in said initial specific activity in the presence of the putative inhibitor.

2. A method of claim 1 wherein the inhibitor induces a decrease of at least 50% in the specific activity of the human GMP synthetase.

3. A method of claim 1 wherein the inhibitor induces a decrease of at least 70% in the specific activity of the human GMP synthetase.

4. A method of claim 1 wherein the inhibitor induces a decrease of at least 90% in the specific activity of the human GMP synthetase.

5. A method of claim 1 wherein inhibition is confirmed via observing the oxidation of NADH.

6. A method of claim 1 wherein inhibition is confirmed via formation of radioactive GMP or AMP from radiolabeled XMP or ATP.

* * * * *

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
        (A) LENGTH: 2237 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (vi) ORIGINAL SOURCE:
        (G) CELL TYPE: Lymphoblast
        (H) CELL LINE: A3.01

(vii) IMMEDIATE SOURCE:
        (B) CLONE: GMPS.6

(xi) SEQUENCE DESCRIPTION: SEQ ID NO:1:

```
GAATTCGGCA CGAGCTCCTC TCCGCTGCCG GCTGCTCCTC GACCAGGCCT CCTTCTCAAC      60

CTCAGCCCGC GGCGCCGACC CTTCCGGCAC CCTCCCGCCC CGTCTCGTAC TGTCGCCGTC     120

ACCGCCGCGG CTCCGGCCCT GGCCCCGATG GCTCTGTGCA ACGGAGACTC CAAGCTGGAG     180

AATGCTGGAG GAGACCTTAA GGATGGCCAC CACCACTATG AAGGAGCTGT TGTCATTCTG     240

GATGCTGGTG CTCAGTACGG GAAAGTCATA GACCGAAGAG TGAGGGAACT GTTCGTGCAG     300

TCTGAAATTT TCCCCTTGGA AACACCAGCA TTTGCTATAA AGGAACAAGG ATTCCGTGCT     360

ATTATCATCT CTGGAGGACC TAATTCTGTG TATGCTGAAG ATGCTCCCTG GTTTGATCCA     420

GCAATATTCA CTATTGGCAA GCCTGTTCTT GGAATTTGCT ATGGTATGCA GATGATGAAT     480

AAGGTATTTG GAGGTACTGT GCACAAAAAA AGTGTCAGAG AAGATGGAGT TTTCAACATT     540

AGTGTGGATA ATACATGTTC ATTATTCAGG GGCCTTCAGA AGGAAGAAGT TGTTTTGCTT     600

ACACATGGAG ATAGTGTAGA CAAAGTAGCT GATGGATTCA AGGTTGTGGC ACGTTCTGGA     660

AACATAGTAG CAGGCATAGC AAATGAATCT AAAAAGTTAT ATGGAGCACA GTTCCACCCT     720

GAAGTTGGCC TTACAGAAAA TGGAAAAGTA ATACTGAAGA ATTTCCTTTA TGATATAGCT     780

GGATGCAGTG GAACCTTCAC CGTGCAGAAC AGAGAACTTG AGTGTATTCG AGAGATCAAA     840

GAGAGAGTAG GCACGTCAAA AGTTTTGGTT TTACTCAGTG GTGGAGTAGA CTCAACAGTT     900
```

```
TGTACAGCTT TGCTAAATCG TGCTTTGAAC CAAGAACAAG TCATTGCTGT GCACATTGAT      960

AATGGCTTTA TGAGAAAACG AGAAAGCCAG TCTGTTGAAG AGGCCCTCAA AAAGCTTGGA     1020

ATTCAGGTCA AAGTGATAAA TGCTGCTCAT TCTTTCTACA ATGGAACAAC AACCCTACCA     1080

ATATCAGATG AAGATAGAAC CCCACGGAAA AGAATTAGCA AAACGTTAAA TATGACCACA     1140

AGTCCTGAAG AGAAAAGAAA AATCATTGGG GATACTTTTG TTAAGATTGC CAATGAAGTA     1200

ATTGGAGAAA TGAACTTGAA ACCAGAGGAG GTTTTCCTTG CCCAAGGTAC TTTACGGCCT     1260

GATCTAATTG AAAGTGCATC CCTTGTTGCA AGTGGCAAAG CTGAACTCAT CAAAACCCAT     1320

CACAATGACA CAGAGCTCAT CAGAAAGTTG AGAGAGGAGG GAAAAGTAAT AGAACCTCTG     1380

AAAGATTTTC ATAAGATGA AGTGAGAATT TTGGGCAGAG AACTTGGACT TCCAGAAGAG      1440

TTAGTTTCCA GGCATCCATT TCCAGGTCCT GGCCTGGCAA TCAGAGTAAT ATGTGCTGAA     1500

GAACCTTATA TTTGTAAGGA CTTTCCTGAA ACCAACAATA TTTTGAAAAT AGTAGCTGAT     1560

TTTTCTGCAA GTGTTAAAAA GCCACATACC CTATTACAGA GAGTCAAAGC CTGCACAACA     1620

GAAGAGGATC AGGAGAAGCT GATGCAAATT ACCAGTCTGC ATTCACTGAA TGCCTTCTTG     1680

CTGCCAATTA AAACTGTAGG TGTGCAGGGT GACTGTCGTT CCTACAGTTA CGTGTGTGGA     1740

ATCTCCAGTA AAGATGAACC TGACTGGGAA TCACTTATTT TTCTGGCTAG GCTTATACCT     1800

CGCATGTGTC ACAACGTTAA CAGAGTTGTT TATATATTTG GCCCACCAGT TAAAGAACCT     1860

CCTACAGATG TTACTCCCAC TTTCTTGACA ACAGGGGTGC TCAGTACTTT ACGCCAAGCT     1920

GATTTTGAGG CCCATAACAT TCTCAGGGAG TCTGGGTATG CTGGGAAAAT CAGCCAGATG     1980

CCGGTGATTT TGACACCATT ACATTTTGAT CGGGACCCAC TTCAAAAGCA GCCTTCATGC     2040

CAGAGATCTG TGGTTATTCG AACCTTTATT ACTAGTGACT TCATGACTGG TATACCTGCA     2100

ACACCTGGCA ATGAGATCCC TGTAGAGGTG GTATTAAAGA TGGTCACTGA GATTAAGAAG     2160

ATTCCTGGTA TTTCTCGAAT TATGTATGAC TTAACATCAA AGCCCCCAGG AACTACTGAG     2220

TGGGAGTAAT AAACTTC                                                    2237
```

(2) INFORMATION FOR SEQ ID NO:2:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:2:

Asn Ile Val Ala Gly Ile Ala Asn Glu Ser Lys
     1          5              10

(2) INFORMATION FOR SEQ ID NO:3:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:3:

Ala Leu Asn Gln Glu Gln Val Ile Ala Val Xaa Ile Asp Asn Gly Phe
       1               5                  10                  15

Met (2) INFORMATION FOR SEQ ID NO:4:

(i) SEQUENCE CHARACTERISTICS:
         (A) LENGTH: 21 amino acids
         (B) TYPE: amino acid
         (C) STRANDEDNESS: single
         (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:4:

Val Ile Asn Ala Ala His Ser Phe Tyr Asn Gly Thr Xaa Xaa Leu Pro
       1               5                  10                  15

Ile Ser Asp Glu Asp
                   20

(2) INFORMATION FOR SEQ ID NO:5:

(i) SEQUENCE CHARACTERISTICS:
         (A) LENGTH: 7 amino acids
         (B) TYPE: amino acid
         (C) STRANDEDNESS: single
         (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:5:

Ile Ile Gly Asp Thr Phe Val
       1               5

(2) INFORMATION FOR SEQ ID NO:6:

(i) SEQUENCE CHARACTERISTICS:
         (A) LENGTH: 14 amino acids
         (B) TYPE: amino acid
         (C) STRANDEDNESS: single
         (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:6:

Val Ile Glu Pro Leu Lys Asp Phe Ile Lys Asp Glu Val Arg
       1               5                  10

(2) INFORMATION FOR SEQ ID NO:7:

(i) SEQUENCE CHARACTERISTICS:
         (A) LENGTH: 14 amino acids
         (B) TYPE: amino acid
         (C) STRANDEDNESS: single
         (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:7:

Val Ile Glu Pro Leu Lys Asp Phe Ile Lys Asp Glu Val Arg
        1               5                  10

(2) INFORMATION FOR SEQ ID NO:8:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:8:

Pro Phe Pro Gly Pro Gly Leu Ala Ile
        1               5

(2) INFORMATION FOR SEQ ID NO:9:

(i) SEQUENCE CHARACTERISTICS:
            (A) LENGTH: 20 amino acids
            (B) TYPE: amino acid
            (C) STRANDEDNESS: single
            (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:9:

Phe Ile Thr Ser Asp Phe Met Thr Gly Ile Pro Ala Thr Pro Gly Asn
        1               5                   10                  15

Glu Ile Xaa Val
                    20

(2) INFORMATION FOR SEQ ID NO:10:

(i) SEQUENCE CHARACTERISTICS:
            (A) LENGTH: 14 amino acids
            (B) TYPE: amino acid
            (C) STRANDEDNESS: single
            (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:10:

Ile Met Tyr Asp Leu Thr Ser Lys Pro Pro Gly Thr Thr Glu
        1               5                   10

(2) INFORMATION FOR SEQ ID NO:11:

(i) SEQUENCE CHARACTERISTICS:
            (A) LENGTH: 693 amino acids

```
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:11:

Met Ala Leu Cys Asn Gly Asp Ser Lys Leu Glu Asn Ala Gly Gly Asp
  1               5                   10                  15

Leu Lys Asp Gly His His His Tyr Glu Gly Ala Val Val Ile Leu Asp
                  20                  25                  30

Ala Gly Ala Gln Tyr Gly Lys Val Ile Asp Arg Arg Val Arg Glu Leu
              35                  40                  45

Phe Val Gln Ser Glu Ile Phe Pro Leu Glu Thr Pro Ala Phe Ala Ile
  50                  55                  60

Lys Glu Gln Gly Phe Arg Ala Ile Ile Ser Gly Pro Asn Ser
  65                  70                  75                  80

Val Tyr Ala Glu Asp Ala Pro Trp Phe Asp Pro Ala Ile Phe Thr Ile
                  85                  90                  95

Gly Lys Pro Val Leu Gly Ile Cys Tyr Gly Met Gln Met Asn Lys
              100                 105                 110

Val Phe Gly Gly Thr Val His Lys Lys Ser Val Arg Glu Asp Gly Val
                  115                 120                 125

Phe Asn Ile Ser Val Asp Asn Thr Cys Ser Leu Phe Arg Gly Leu Gln
  130                 135                 140

Lys Glu Glu Val Val Leu Leu Thr His Gly Asp Ser Val Asp Lys Val
  145                 150                 155                 160

Ala Asp Gly Phe Lys Val Val Ala Arg Ser Gly Asn Ile Val Ala Gly
                  165                 170                 175

Ile Ala Asn Glu Ser Lys Lys Leu Tyr Gly Ala Gln Phe His Pro Glu
              180                 185                 190

Val Gly Leu Thr Glu Asn Gly Lys Val Ile Leu Lys Asn Phe Leu Tyr
                  195                 200                 205

Asp Ile Ala Gly Cys Ser Gly Thr Phe Thr Val Gln Asn Arg Glu Leu
  210                 215                 220

Glu Cys Ile Arg Glu Ile Lys Glu Arg Val Gly Thr Ser Lys Val Leu
  225                 230                 235                 240

Val Leu Leu Ser Gly Gly Val Asp Ser Thr Val Cys Thr Ala Leu Leu
                  245                 250                 255

Asn Arg Ala Leu Asn Gln Glu Gln Val Ile Ala Val His Ile Asp Asn
              260                 265                 270

Gly Phe Met Arg Lys Arg Glu Ser Gln Ser Val Glu Glu Ala Leu Lys
                  275                 280                 285

Lys Leu Gly Ile Gln Val Lys Val Ile Asn Ala Ala His Ser Phe Tyr
  290                 295                 300

Asn Gly Thr Thr Thr Leu Pro Ile Ser Asp Glu Asp Arg Thr Pro Arg
  305                 310                 315                 320

Lys Arg Ile Ser Lys Thr Leu Asn Met Thr Thr Ser Pro Glu Glu Lys
                  325                 330                 335

Arg Lys Ile Ile Gly Asp Thr Phe Val Lys Ile Ala Asn Glu Val Ile
              340                 345                 350

Gly Glu Met Asn Leu Lys Pro Glu Glu Val Phe Leu Ala Gln Gly Thr
                  355                 360                 365

Leu Arg Pro Asp Leu Ile Glu Ser Ala Ser Leu Val Ala Ser Gly Lys
```

-continued

```
                        370                     375                     380
            Ala Glu Leu Ile Lys Thr His His Asn Asp Thr Glu Leu Ile Arg Lys
            385                     390                     395                     400

Leu Arg Glu Glu Gly Lys Val Ile Glu Pro Leu Lys Asp Phe His Lys
                                405                     410                     415

Asp Glu Val Arg Ile Leu Gly Arg Glu Leu Gly Leu Pro Glu Glu Leu
                            420                     425                     430

Val Ser Arg His Pro Phe Pro Gly Pro Gly Leu Ala Ile Arg Val Ile
                            435                     440                     445

Cys Ala Glu Glu Pro Tyr Ile Cys Lys Asp Phe Pro Glu Thr Asn Asn
                    450                     455                     460

Ile Leu Lys Ile Val Ala Asp Phe Ser Ala Ser Val Lys Lys Pro His
            465                     470                     475                     480

Thr Leu Leu Gln Arg Val Lys Ala Cys Thr Thr Glu Glu Asp Gln Glu
                                485                     490                     495

Lys Leu Met Gln Ile Thr Ser Leu His Ser Leu Asn Ala Phe Leu Leu
                            500                     505                     510

Pro Ile Lys Thr Val Gly Val Gln Gly Asp Cys Arg Ser Tyr Ser Tyr
                            515                     520                     525

Val Cys Gly Ile Ser Ser Lys Asp Glu Pro Asp Trp Glu Ser Leu Ile
                    530                     535                     540

Phe Leu Ala Arg Leu Ile Pro Arg Met Cys His Asn Val Asn Arg Val
            545                     550                     555                     560

Val Tyr Ile Phe Gly Pro Pro Val Lys Glu Pro Pro Thr Asp Val Thr
                                565                     570                     575

Pro Thr Phe Leu Thr Thr Gly Val Leu Ser Thr Leu Arg Gln Ala Asp
                            580                     585                     590

Phe Glu Ala His Asn Ile Leu Arg Glu Ser Gly Tyr Ala Gly Lys Ile
                            595                     600                     605

Ser Gln Met Pro Val Ile Leu Thr Pro Leu His Phe Asp Arg Asp Pro
                    610                     615                     620

Leu Gln Lys Gln Pro Ser Cys Gln Arg Ser Val Val Ile Arg Thr Phe
            625                     630                     635                     640

Ile Thr Ser Asp Phe Met Thr Gly Ile Pro Ala Thr Pro Gly Asn Glu
                                645                     650                     655

Ile Pro Val Glu Val Val Leu Lys Met Val Thr Glu Ile Lys Lys Ile
                            660                     665                     670

Pro Gly Ile Ser Arg Ile Met Tyr Asp Leu Thr Ser Lys Pro Pro Gly
                            675                     680                     685

Thr Thr Glu Trp Glu
                    690
```